(12) United States Patent
Ouyang et al.

(10) Patent No.: US 11,495,448 B2
(45) Date of Patent: *Nov. 8, 2022

(54) SYSTEMS AND METHODS FOR QUANTIFYING AN ANALYTE EXTRACTED FROM A SAMPLE

(71) Applicant: Purdue Research Foundation, West Lafayette, IN (US)

(72) Inventors: Zheng Ouyang, West Lafayette, IN (US); Yue Ren, West Lafayette, IN (US); Ziqing Lin, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 99 days.

This patent is subject to a terminal disclaimer.

(21) Appl. No.: 16/985,553

(22) Filed: Aug. 5, 2020

(65) Prior Publication Data
US 2020/0381239 A1    Dec. 3, 2020

Related U.S. Application Data

(63) Continuation of application No. 16/293,017, filed on Mar. 5, 2019, now Pat. No. 10,777,402, which is a
(Continued)

(51) Int. Cl.
*H01J 49/04* (2006.01)
*H01J 49/16* (2006.01)
*C12Q 1/6806* (2018.01)

(52) U.S. Cl.
CPC .......... *H01J 49/167* (2013.01); *C12Q 1/6806* (2013.01); *Y10T 436/24* (2015.01); *Y10T 436/255* (2015.01)

(58) Field of Classification Search
CPC ...... H01J 49/0468; H01J 49/167; H01J 49/00; H01J 49/0013; H01J 49/0027; H01J 49/04;
(Continued)

(56) References Cited

U.S. PATENT DOCUMENTS 3,615,170 A   10/1971  Hazen et al.
4,298,795 A   11/1981  Takeuchi et al.
(Continued)

FOREIGN PATENT DOCUMENTS

JP   2005/503557 A   2/2005
JP   2006/300946 A   11/2006
(Continued)

OTHER PUBLICATIONS

Silber, 1954, The Determination of 17, 21-Dihydroxy-20-ketosteroids in Urine and Plasm, Journal of Biological Chemistry, 210, 923-932.
(Continued)

*Primary Examiner* — Maureen Wallenhorst
(74) *Attorney, Agent, or Firm* — Brown Rudnick LLP

(57) ABSTRACT

The invention generally relates to systems and methods for quantifying an analyte extracted from a sample. In certain embodiments, the invention provides methods that involve introducing a solvent into a capillary, introducing the capillary into a vessel including a sample such that a portion of the sample is introduced into the capillary, moving the sample and the solvent within the capillary to induce circulation within the sample and the solvent, thereby causing the analyte to be extracted from the sample and into the solvent, analyzing the analyte that has been extracted from the sample, and quantifying the analyte. In certain embodiments, the quantifying step is performed without knowledge of a volume of the sample and/or solvent.

20 Claims, 26 Drawing Sheets

Related U.S. Application Data continuation of application No. 15/064,865, filed on Mar. 9, 2016, now Pat. No. 10,269,550, which is a continuation-in-part of application No. PCT/US2015/013649, filed on Jan. 30, 2015.

(60) Provisional application No. 62/130,024, filed on Mar. 9, 2015, provisional application No. 62/013,007, filed on Jun. 17, 2014, provisional application No. 61/492,949, filed on Feb. 21, 2014.

(58) Field of Classification Search
CPC ............... Y10T 436/24; Y10T 436/25; Y10T 436/25375; Y10T 436/255; Y10T 436/2575; G01N 1/18; G01N 27/62; G01N 30/72; C12Q 1/6806
USPC ........ 436/173, 174, 177, 178, 180; 422/527; 536/25.41
See application file for complete search history.

(56) References Cited

U.S. PATENT DOCUMENTS

| | | | |
|---|---|---|---|
| 4,399,102 | A | 8/1983 | Karlberg et al. |
| 6,229,046 | B1 * | 5/2001 | Eyal ..................... C07C 67/08 562/580 |
| 6,337,480 | B1 | 1/2002 | Andrien, Jr. et al. |
| 6,501,073 | B1 | 12/2002 | Mylchreest et al. |
| 8,410,431 | B2 | 4/2013 | Ouyang et al. |
| 10,008,375 | B2 * | 6/2018 | Ouyang .............. H01J 49/0459 |
| 10,269,550 | B2 * | 4/2019 | Ouyang ............... C12Q 1/6806 |
| 10,559,456 | B2 * | 2/2020 | Ouyang .............. H01J 49/0431 |
| 10,777,402 | B2 * | 9/2020 | Ouyang ............... C12Q 1/6806 |
| 11,060,959 | B2 * | 7/2021 | Ouyang ................. B01D 15/10 |
| 2006/0118713 | A1 | 6/2006 | Matsui et al. |
| 2010/0282962 | A1 | 11/2010 | Machuron-Mandard et al. |
| 2012/0085900 | A1 | 4/2012 | Verbeck, IV |
| 2013/0280819 | A1 | 10/2013 | Cooks et al. |
| 2014/0284284 | A1 | 9/2014 | Troost |
| 2016/0126080 | A1 | 5/2016 | Kertesz et al. |

FOREIGN PATENT DOCUMENTS

| | | |
|---|---|---|
| JP | 2009/534806 A | 9/2009 |
| JP | 2019038269 A | 3/2019 |
| WO | 2010/127059 A1 | 11/2010 |
| WO | 2014195662 A1 | 12/2014 |

OTHER PUBLICATIONS

Soko, 2011, Miniature mass spectrometer equipped with electrospray and desorption electrospray ionization for direct analysis of organics from solids and solutions, Int. J Mass Spectrom., vol. 306, 182-195.
Soloshonok, 2017, Why is chloroform a non-polar solvent?, 1 page.
WADA Laboratory Executive Committee—TD2014EAAS, Endogenous Anabolic Androgenic Steroids Measurement and Reporting WADA Technical Document 2004, 9 pages.
Wang, 2010, Paper Spray for Direct Analysis of Complex Mixtures Using Mass Spectrometry, Angewandte Chemie-International Edition, 49, 877-880.
Wannamethee, 1997, Serum Creatinine Concentration and Risk of Cardiovascular Disease, A Possible Marker for Increased Risk of Stroke, Stroke, 28, 557-563.
Xu, 2010, Miniaturization of Mass Spectrometry Analysis Systems, JALA Charlottesv Va., 15(6):433-439.
Yates, 2011, A centrury of mass spectrometry: from atoms to proteomes, Nature Methods, 8(8):633-637.
Yuan, 2013, A rugged and accurate liquid chromatography-tandem mass spectrometry method for the determination of asunaprevir, an NS3 protease inhibitor, in plasma, Journal of Chromatography B, vol. 921-922, 81-86.
Zhao, 2006, Liquid-liquid two-phase flow patterns in a rectangular microchannel, AIChE Journal, 52(12):4052-4060.
Zhu, 2000, Formation and Decompositions of Chloride Adduct Ions, [M +Cl]−, in Negative Ion Electrospray Ionization Mass Spectrometry, J Am. soc. Mass Spectrom., 11, 932-941.
Bruzewicz, 2008, Low-Cost Printing of Poly(dimethylsiloxane) Barrers to Define Microchannels in Paper, Anal Chem., vol. 80, 3387-3392.
Burns, 2001, The intensification of rapid reactions in multiphase systems using slug flow in capillaries, Lab on a Chip, 1, 10-15.
Cai, 1996, On-Line Immunoaffinity Extraction-Coupled Column Capilllary Liquid Chromatography/Tandem Mass Spectrometry: Trace Analysis of LSD analogs and Metabolites in Human Urine, Anal. Chem., vol. 68, 72-78.
Carlsson, 2000, Monosegmented micro-volume liquid-liquid flow-extraction system based on intermittent pumping and spectroscopic detection, Analytica Chimica Acta, vol. 415, No. 1-2.
Casari, 2001, Application of solvent microextraction to the analysis of amphetamines and phencyclidine in urine, Forensic Science International, 120, 165-171.
Chace, 2001, Mass Spectrometry in the Clinical Laboratory, Chemical Reviews, 101, 445-477.
Cooks, 2006, Ambient Mass Spectrometry, www.sciencemag.org, vol. 311, Mar. 17, 2006, 1566-1570.
Department of Defese Instruction 1010.16 "Technical Procedures for the Military Personnel Drug Abuse Testing Program", 2012, http://www.dtic.mil/whs/directives/corres/pdf/101016p.pdf.
Dewan, 2008, Mass ethion poisoning with high mortality, Clinical Toxicology, 46, pp. 85-88.
El-Faramawy, 2005, Efficiency of Nano-Electrospray Ionization, J Am Soc Mass Spectrom, vol. 16, pp. 1702-1707.
English translation of Office Action issued in Japanese Application No. JP 2016-552897, dated Sep. 7, 2017, 8 pages.
Extended European Search Report for European Application No. EP 15752801.9, dated Sep. 11, 2017, 9 pages.
Fico, 2007, Miniaturization and Geometry Optimization of a Polymer-Based Rectilinear Ion Trap, Anal. Chem., 79:8076-8082.
Gao, 2006, "Handheld Rectilinear Ion Trap Mass Spectrometer," (Anal. Chem., 78, 5994-6002.
Gao, 2008, Design and Characterization of a Multisource Hand-Held Tandem Mass Spectrometer, Anal. Chem., 80, 7198-7205.
Gao, 2009, Characterization of a discontinuous atmospheric pressure interface. Multiple ion introduction pulses for improved performance. International Journal of Mass Spectrometry, vol. 283, No. 1-3, 30-34.
Horn, 2012, On-stage liquid-phase lipid microextraction coupled to nanospray mass spectrometry for detailed, nano-scale lipid analysis, Rapid Commun. Mass Spectrom., vol. 26, 957-962.
Hou, 2011, Sampling Wand for an Ion Trap Mass Spectrometer, Anal. Chem, 83:1857-1861.
Huang, 2007, Rapid Screening of Anabolic Steriods in Urine by Reactive Desorption Electrospray Ionization, Analytical Chemistry , 79, 8327-8332.
Indiana State Department of Toxicology Testing Sumary, 2014, http://www.in.gov/isdt/files/Screen-conf-list-2014.pdf.
International Preliminary Report on Patentability issued in International Application No. PCT/US2015/013649, dated Sep. 1, 2016, 8 pages.
International Search Report and Written Opinion for International Application No. PCT/US2015/013649, dated Jun. 17, 2015, 15 pages.
Jovanovic, 2011, Liquid-liquid slug flow: Hydrodynamics and pressure drop, Chemical Engineering Science, 66, 42-54.
Kalhorn, 2007, Analysis of testosterone and dihydrotestosterone from biological fluids as the oxime derivatives using high-performance liquid chromatography/tandem mass spectrometry, Rapid Communications in Mass Spectrometry, 21, 3200-3206.
Karas, 2000, Nano-electrospray ionization mass spectrometry: addressing analytical problems beyond routine, Fresenius J Anal Chem, vol. 366, 669-676.
Kashid, 2007, Liquid-Liquid Slug Flow in a Capillary: An Alternative to Suspended Drop or Film Contractors, Ind. Eng. Chem. Res., vol. 46, 8420-8430.

(56) References Cited

OTHER PUBLICATIONS

Li, 2008, Paper-Based Microfluidic Devices by Plasma Treatment, Anal. Chem., vol. 80, 9131-9134.
Li, 2014, Mini 12, Miniature Mass Spectrometer for Clinical and Other Applications—Introduction and Characterization, Analytical Chemistry, 86, 2909-2916.
Lindenburg, 2010, Online capillary liquid-liquid electroextraction of peptides as fast pre-concentration prior to LC-MS, Electrophoresis, vol. 31, 3903-3912.
Liu, 2013, Enabling Quantitative Analysis in Ambient Ionization Mass Spectrometry: Internal Standard Coated Capillary Samplers, Analytical Chemistry, 85, 5632-5636.
Martinez, 2007, Patterned Paper as a Platform for Inexpensive, Low-Volume, Portable Bioassays, Angew. Chem. Int. Ed., vol. 46, 1318-1320.
Martinez, 2008, Flash: A rapid method for prototyping paper-based microfluidic devices, Lab Chip, vol. 8, 2146-2150.
Martinez, 2008, Three-dimensional microfluidic devices fabricated in layered paper and tape, Proc. Natl Acad. Sci. USA, vol. 105, No. 50, 19606-19611.
Monge, 2013, Mass Spectrometry: Recent Advances in DIrect Open Air Surface Sampling/Ionization, Chem. Rev., vol. 113, 2269-2308.
Mulligan, 2006, Desorption electrospray ionization with a portable mass spectrometer: in situ analysis of ambient surfaces, Chem. Commun., 1709-1711.
Nakanishi, 1985, Continuous Synthesis of N-(Benzyloxycarbonyl)-L-Aspartyl-L-Phenylalanine Methyl Ester with Immobilized Thermolysin in an Organic Solvent, Bio-Technology, vol. 3, 459-464.
Office Action and English translation of same, issued in Chinese Application No. 201580008376.X, dated May 31, 2017, 19 pages.
Office Action and English translation of the same, issued in Japanese Application No. 2016-195522, dated Aug. 28, 2017, 6 pages.
Office Action issued in CN application No. 201580008376.X, dated Aug. 17, 2018, 5 pages.
Office Action issued in European Application No. EP 15752801.9, dated Dec. 19, 2018, 6 pages.
Office Action issued in Japanese Patent Application No. 2019-038269, dated Dec. 26, 2019, 5 pages.
Office Action issued in U.S. Appl. No. 15/064,865, dated Dec. 1, 2017, 15 pages.
Ouyang, 2009, Handheld Miniature Ion Trap Mass Spectrometers, Anal. Chem., vol. 81, 2421-2425.
Ouyang, 2009, Miniature Mass Spectrometers, Ann. Rev. Anal. Chem., vol. 2, 187-214.
Regenthal, 1999, Drug Levels: Therapeutic and Toxic Serum/Plasma Concentrations of Common Drugs, J Clin Monit Comput, 15, 529-544.
Ren, 2014, Direct Mass Spectrometry Analysis of Biofluid Samples Using Slug-Flow Microextraction Nano-Electrospray Ionization, Angewandte Chemie International Edition, 53( 51):14124-14127.
Rogers, 1996, The Efficacy and Safety of Donepezil in Patients with Alzheimer's Disease: Results of a US Multicentre, Randomized, Double-Blind, Placebo-Controlled Trial, Dementia, vol. 7, 293-303.
Rojas-Leon, 2011, Solvent-solvent and solvent-solute interactions in a 3D chloroform clathrate with diorganotin macrocycles in the nano-sized pores, Chemical Communications, UK, 48(3)401-403.
Sanders, 2009, Hand-held Mass Spectrometer for Environmentally Relevant Analytes Using a Variety of Sampling and Ionization Methods, Euro. J. Mass Spectrom., vol. 16, 11-20.
Serrano, 2011, Micro liquid-liquid extraction combined with large-volume injection as chromatography-mass spectrometry for the determination of haloacetaldehydres in treated water, J. Chromoatogr. A, 1218:8295-8302.

* cited by examiner

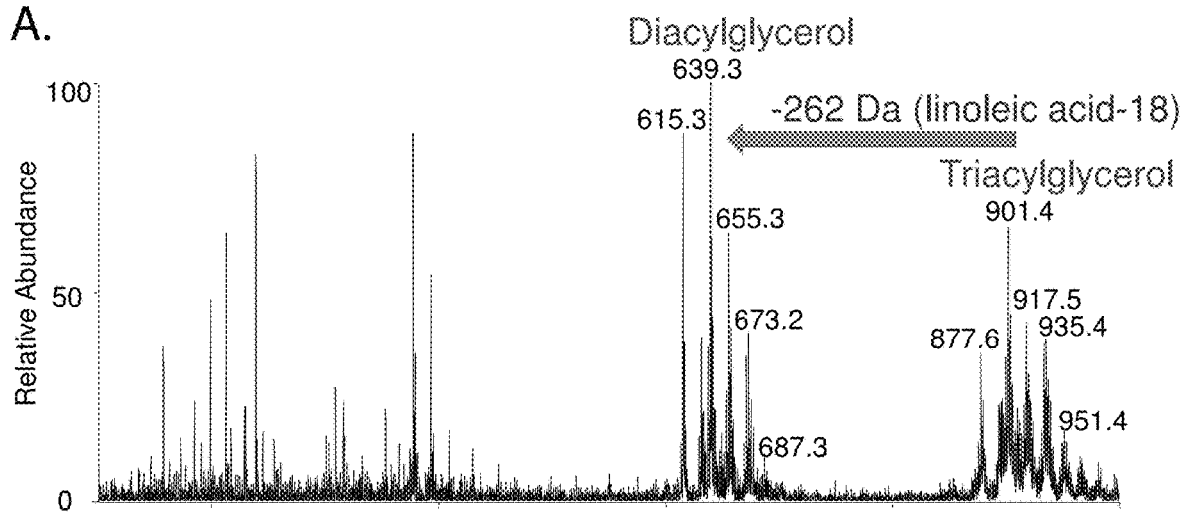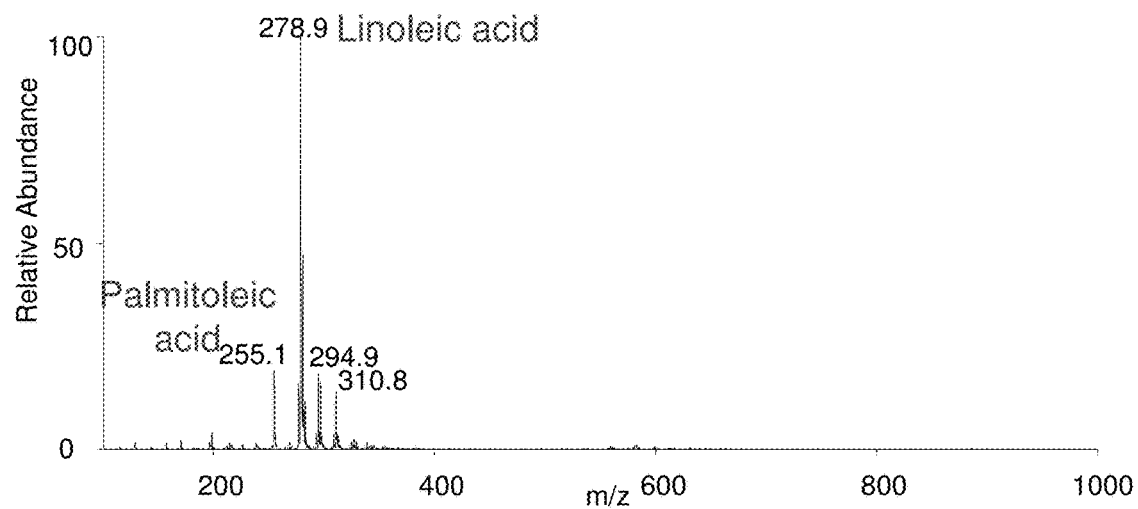
FIG. 8

Before extraction:

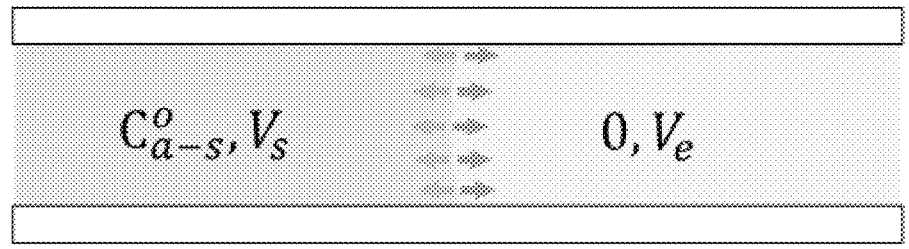

After reaching the extraction equilibrium:

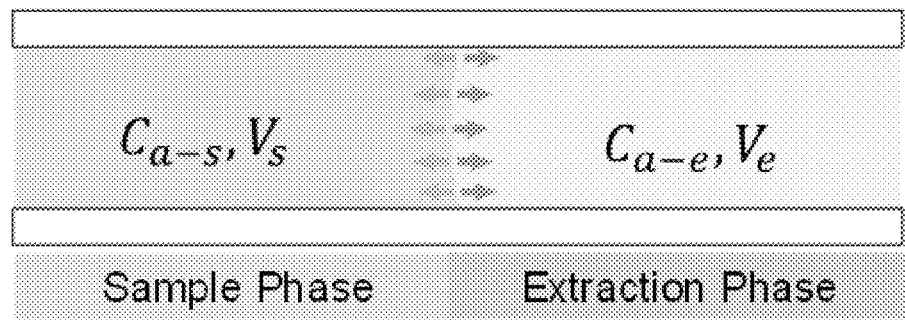

As shown in the above scheme, in a two-phase fluidic system with a phase volume of $V_s$ and $V_e$, respectively, an analyte amount and concentration before and after the extraction in the two phases can be noted as $C^o_{a-s}/C_{a-s}$ (sample phase), and $0/C_{a-e}$ (extraction phase) respectively.

$$C^o_{a-s} V_s = C_{a-s} V_s + C_{a-e} V_e$$

Defining D as $C_{a-s} = D \cdot C_{a-e}$, then $$C^o_{a-s} V_s = D \cdot C_{a-s} V_s + C_{a-e} V_e$$

Thus, $$C_{a-e} = \frac{V_s}{D \cdot V_s + V_e} \cdot C^o_{a-s}$$

FIG. 14A

Before extraction:

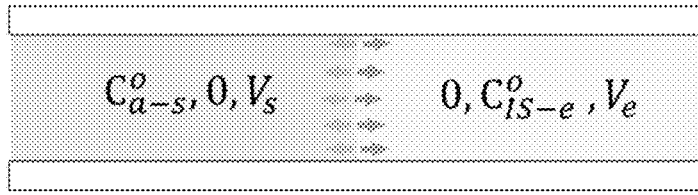

After reaching the extraction equilibrium:

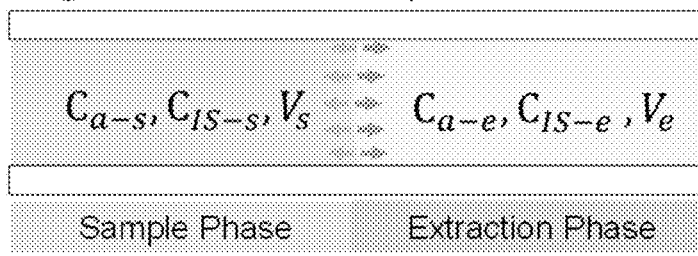

According to Eq. 1, after reaching the equilibrium point, the concentration of an analyte and its internal standard in the extraction phase can be defined as the equation below:

$$I_a = k_a \cdot C_{a-e} = \frac{V_s}{D \cdot V_s + V_e} \cdot C^0_{a-s}$$

$$I_{IS} = k_{IS} \cdot C_{IS-e} = \frac{V_e}{D \cdot V_s + V_e} \cdot C^0_{IS-e}$$

where $k_a / k_{IS}$ is the response factor of the signal intensity to an analyte/ internal standard concentration for an mass spectrometer; $C^0_{IS-e}$ and $C_{IS-e}$ is the internal standard concentration in the extraction phase before and after the extraction; $C_{IS-s}$ is the internal standard concentration in the sample phase after the extraction. At the equilibrium condition, the analyte-internal standard intensity ratio can be defined as:

$$\frac{I_a}{I_{IS}} = \frac{k_a}{k_{IS}} \cdot \frac{C_{a-e}}{C_{IS-e}} = \frac{k_a}{k_{IS}} \cdot \frac{V_s}{C^0_{IS-e} V_e} \cdot C^0_{a-s}$$

FIG. 14B

Summary of the target ions for MS/MS analysis of steroid using reactive SFME-nanoESI.

| Steroids | Molecular Ion (m/z) | Product Ion (m/z) | Monitored Ion (m/z) |
|---|---|---|---|
| Epitestosterone | 289 | 304 | 124 |
| 6-Dehydrocholestenone | 383.6 | 398.1 | 203.9 |
| 5α-Androstan-3β,17β-Diol-16-one | 307 | 322 | 102 |
| Stigmastadienone | 429 | 411.7 | 83.4 |

LODs obtained with SLME nanoESI and cut-off concentrations for detection or monitoring

| Compound | Sample | Derivatization | Sample volume (µL) | LOD (ng/mL)[b] | Cut-off Value (ng/mL) |
|---|---|---|---|---|---|
| Methamphetamine | urine | NA | 5 | 0.03 | 100[3] |
| | blood[a] | NA | 5 | 0.1 | 20[4] |
| Benzoylecgonine | urine | NA | 5 | 0.1 | 150[3] |
| | blood[a] | NA | 5 | 1 | 50[4] |
| Verapamil | blood[a] | NA | 5 | 0.05 | 50[5] |
| Amitripyline | blood[a] | NA | 5 | 0.08 | 50[5] |
| Epitestosterone | urine | Hydroxyl-amine | 5 | 0.7 | 50[6] |
| 6-Dehydro-cholestenone | urine | Hydroxyl-amine | 5 | 0.6 | N/A |
| 5α–Androstan-3β, 17β–Diol-16-one | urine | Hydroxyl-amine | 5 | 0.2 | N/A |
| Stigmastadienone | urine | Hydroxyl-amine | 5 | 0.8 | N/A |

[a] Blood samples undiluted.

[b] The limits of detection were determined as the concentrations for which the signal response is 3 times of the noise from blank in SRM mode.

FIG. 22

SYSTEMS AND METHODS FOR QUANTIFYING AN ANALYTE EXTRACTED FROM A SAMPLE

RELATED APPLICATION

The present application is a continuation of U.S. nonprovisional application Ser. No. 16/293,017, filed Mar. 5, 2019, now U.S. Pat. No. 10,777,402, which is a continuation of U.S. nonprovisional application Ser. No. 15/064,865, filed Mar. 9, 2016, now U.S. Pat. No. 10,269,550, which is a continuation-in-part of PCT/US15/13649, filed Jan. 30, 2015, which claims the benefit of and priority to U.S. provisional patent application Ser. No. 61/942,949, filed Feb. 21, 2014, and U.S. provisional patent application Ser. No. 62/013,007, filed Jun. 17, 2014. The present application also claims the benefit of and priority to U.S. provisional application Ser. No. 62/130,024, filed Mar. 9, 2015. The content of each of these applications is incorporated by reference herein in its entirety.

GOVERNMENT SUPPORT

This invention was made with government support under GM106016 awarded by the National Institutes of Health. The government has certain rights in the invention.

FIELD OF THE INVENTION

The invention generally relates to systems and methods for quantifying an analyte extracted from a sample.

BACKGROUND

Rapid analysis of complex biological samples (e.g., complex mixtures such as blood, saliva, or urine) is of significant interest for clinical, forensic and many other applications. A problem in the analysis of such samples using mass spectrometry is that non-target components of a biological sample (e.g., salts), compete with a target in the sample for charges during the ionization process. That competition leads to the non-target components of the sample suppressing ionization of the target in the sample, known as matrix effects. In order to minimize suppression effects on analyte ionization and to pre-concentrate the analytes, complex biological samples are routinely extracted and then separated using chromatography before a mass spectrometry measurement. However, such a process can only be conducted in a laboratory setting using expensive chromatography equipment and time consuming sample preparation protocols.

SUMMARY

The invention provides a new approach for liquid-liquid extractions and also provides systems and methods that allow for sample preparation and pre-treatment to be combined with the ionization process. Particularly, the invention allows for a liquid-liquid extraction to be conducted in a capillary of very small diameter, which provides a very small interface between the two liquids (e.g., capillary of inner diameter as small as 500 um). That is typically considered highly unfavorable for traditional liquid-liquid extractions. The liquid in the capillary is moved back and forth, which allows for control of the extraction process, i.e., the extraction can be turned on and off. The motion induces circulation inside each plug of immiscible fluid, which facilitates the extraction. The added benefits for using the thin capillary are that small amounts of samples (e.g., large volume samples of greater than 100 μl) can be handled for analysis and further for quantitative analysis.

Additionally, it is possible for the extraction capillary to serve as an ionization probe. In that manner, the invention provides systems and methods that allow a target analyte in a sample to be extracted and analyzed by mass spectrometry without conducting separate sample preparation and pre-treatment protocols. Rather, systems and methods of the invention are configured so that sample preparation and pre-concentration are conducted within the ionization probe. The purified analyte can then be directly ionized (although not required) and injected into a mass spectrometer from the ionization probe in which the sample preparation and pre-treatment occurred.

In certain embodiments, aspects of the invention are accomplished using a solvent that is immiscible with the sample. A solvent is introduced into a capillary. The capillary is introduced into a vessel including a sample such that a portion of the sample is introduced into the capillary. The sample and the solvent are moved within the capillary to induce circulation within the sample and the solvent, thereby causing the analyte to be extracted from the sample and into the solvent. The methods of the invention can be performed with any volume of sample. Methods of the invention may additionally involve quantifying the analyte. In certain embodiments, the quantifying step is performed without knowledge of a volume of the sample. In certain embodiments, the sample is a large volume sample (e.g., a sample having a volume greater than 100 μl).

In embodiments in which the extraction capillary also serves as the ionization probe, an electrode is then operably coupled to the solvent within the body of the ionization probe (capillary) and the target analyte is ionized and injected into the mass spectrometer. In that manner, sample preparation and pre-treatment are combined with the ionization process, and when voltage is applied to the solvent, the target analyte does not need to compete with the non-target components of the sample (e.g., salts in urine) for charges. According to such embodiments, systems and methods of the invention effectively suppress matrix effects, and allow for better ionization of target analytes from samples, particularly biological samples, such as blood, saliva, urine, or spinal cord fluid. Systems and methods of the invention also have the added benefit of pre-concentrating target analytes from a sample into the extraction solvent, thereby avoiding expensive chromatography equipment and time consuming separation protocols, and enabling point-of-care sample analysis systems and methods.

One of skill in the art will recognize that the order in which the sample and the solvent are introduced to the hollow body (e.g., capillary) does not matter. In certain embodiments, the solvent is introduced first and the sample is introduced second. In other embodiments, the sample is introduced first and the solvent is introduced second. In certain embodiments, the sample and the solvent are immiscible. In certain embodiments, more than one solvent is used. For example, a second solvent can be introduced that sits between the first solvent and the sample (three phase embodiments). The second solvent can act as a solvent bridge, and is immiscible with the sample and the first solvent, which are typically miscible with each other in such an embodiment.

In certain embodiments, the sample and the solvent are gently mixed prior to application of the voltage. That can be conducted manually, by gently tilting the capillary, or through use of a moving mechanism. In certain embodiments, the two or more phases do not mix with each other. An exemplary moving mechanism is a pump that applies altering pneumatic forces within the hollow body to push and pull the sample within the body, thereby causing gentle movements. In certain embodiments, a high voltage was applied to the solvent eject the solvent from the hollow body, desolvate and ionize the sample. In other embodiments, a nebulizing gas is also applied to the extracted sample, either pulsed or as a continuous flow.

Methods of the invention can be used with any type of sample. In certain embodiments, the sample is a biological fluid, such as blood, urine, saliva, or spinal cord fluid. The sample will typically include a target of interest. In the case of biological samples, that target may be a therapeutic drug, a drug of abuse, or other molecule, such as a steroid. The target may be a component that is native to the sample, or one that has been artificially introduced to the sample. In certain embodiments, an internal standard is also introduced.

In certain embodiments, the target to be analyzed is a target that is not efficiently ionized, for example, by spray ionization. In such embodiments, it is beneficial to derivatize the target molecule by introduce an agent that is able to impart a charged group to the target, thereby making it more amenable to ionization. For example, steroids are difficult to ionize by spray ionization. Introducing an agent to the sample, such as hydroxylamine, imparts a charged group to the steroid, making it amenable to spray ionization.

The extraction solvent chosen will depend on the target to be extracted. It is important to also consider the effectiveness of the solvent for ionization. An ideal solvent is good for both extraction and ionization. Such an exemplary solvent is ethyl acetate, although the skilled artisan will recognize that other solvents are also effective to both extract and ionize a target in a sample. In embodiments in which multiple analytes are extracted from the sample into the solvent, the solvent may also be able to differentially extract the analytes.

Numerous methods exist for analyzing the ions. In certain embodiments, analyzing involves introducing the ions to a mass analyzer of a mass spectrometer or a miniature mass spectrometer. An exemplary miniature mass spectrometer is described, for example in Gao et al. (Anal. Chem. 2008, 80, 7198-7205), the content of which is incorporated by reference herein in its entirety. In comparison with the pumping system used for lab-scale instruments with thousands watts of power, miniature mass spectrometers generally have smaller pumping systems, such as a 18 W pumping system with only a 5 L/min (0.3 m3/hr) diaphragm pump and a 11 L/s turbo pump for the system described in Gao et al. Other exemplary miniature mass spectrometers are described for example in Gao et al. (Anal. Chem.,2006, 80:7198-7205, 2008), Hou et al. (Anal. Chem., 83:1857-1861, 2011), and Sokol et al. (Int. J. Mass Spectrom., 2011, 306, 187-195), the content of each of which is incorporated herein by reference in its entirety.

Other aspects of the invention provide systems for analyzing an analyte in a sample. The system includes an ionization probe and a mass spectrometer. As mentioned above, the mass spectrometer may be a bench-top mass spectrometer or a miniature mass spectrometer. The ionization probe includes a hollow body that includes a distal tip (e.g., a glass capillary stretched to a tip). The hollow body is configured such that there is no substrate within the body and no electrode disposed on a surface of the body. Rather, an electrode is at least partially disposed within the hollow body. In certain embodiments, the electrode is spaced from the surfaces of the hollow body, i.e., does not touch the surfaces of the hollow body. In certain embodiments, the electrode is coaxially disposed within the hollow body. In certain embodiments, the electrode extends to a distal portion of the hollow body. An exemplary electrode is a metal wire.

In certain embodiments, the probe operates without pneumatic assistance. In other embodiments, the system includes a source of nebulizing gas. The source of nebulizing gas may be configured to provide pulses of gas or may be configured to provide a continuous flow of gas.

In other aspects, the invention provides methods for extracting an analyte from a sample. Those methods involve introducing a solvent into a capillary. A sample including an analyte is also introduced into the capillary. In certain embodiments, the solvent does not mix with the sample. In other embodiments, the solvent and the sample to mix with each other. The sample and the solvent are moved within the capillary to induce circulation within the sample and the solvent, thereby causing the analyte to be extracted from the sample and into the solvent. In certain embodiments, the solvent is introduced first and the sample is introduced second. In other embodiments, the sample is introduced first and the solvent is introduced second. In certain embodiments, the sample and the solvent are immiscible. In certain embodiments, more than one solvent is used. For example, a second solvent can be introduced that sits between the first solvent and the sample (three phase embodiments using a bridging solvent). The second solvent can act as a solvent bridge, and is immiscible with the sample and the first solvent, which are typically miscible with each other in such an embodiment.

In certain embodiments, the methods may additionally involve analyzing the extracted analyte. Analyzing may involve applying a voltage to the solvent comprising the extracted analyte in the capillary so that the analyte is expelled from the capillary, thereby generating ions of the analyte, and analyzing the ions. In other embodiments, analyzing may involve removing the solvent comprising the extracted analyte from the capillary, and conducting an assay that analyzes the analyte.

Methods of the invention allow for the reactions to be monitored. To monitor the reaction, the methods may additionally involve stopping movement of the sample and the solvent within the capillary, and analyzing an amount of analyte that has been extracted into the solvent. Based on the results of the analyzing step, the methods of the invention may additionally involve re-starting movement of the sample and the solvent within the capillary based on results of the analyzing step.

Another aspect of the invention provides methods for extracting an analyte from a sample that involve introducing multiple solvents into a capillary, in which each two adjacent solvents do not mix with each other, and moving the solvents within the capillary to induce circulation within each solvent, thereby causing the chemical compounds to be transferred between the solvents.

BRIEF DESCRIPTION OF THE DRAWINGS

FIG. 2 panel A shows methamphetamine. FIG. 2 panel B shows nicotine. FIG. 2 panel C shows benzoylecgonine. 10 μL synthetic urine containing the drugs and internal standards were used as samples for the measurement. 5 μL ethyl acetate (EA) was used as the extraction phase for extraction, purification and spray. Internal standards: methamphetamine-d8 at 0.8 ng/mL, nicotine-d32 at ng/mL, benzoylecgonine-d3 at 1 ng/mL. The single reaction monitoring (SRM) transitions used: methamphetamine m/z 150→91, methamphetamine-d8 m/z 158→93; nicotine 163→130, nicotine-d3 m/z 166→130; benzoylecgonine m/z 290→168, benzoylecgonine-d3 m/z 293→171. Partition coefficients: LogPmethamphetamine=2.07; LogPnicotine=1.17, LogPbenzoylecgonine=−0.59.

FIG. 8 panels A-B shows analysis of vegetable oil using systems and methods of the invention. A mixture of water and methanol was used as the extraction solvent. FIG. 8 panel A is an MS spectrum showing that diacylglycerol and triacylglycerol species were observed in the MS spectrum in positive mode. FIG. 8 panel B is an MS spectrum showing that different fatty acids were observed in the MS spectrum acquired in negative mode.

FIG. 9 panel A shows an MS spectrum of a 5 μL sample that was 10× diluted using methanol as reduction of matrix and sprayed directly by nanoESI. FIG. 9 panel B shows an MS spectrum of a 5 μL sample that was processed by 3-phase SFME with hexane/$H_2O$:MeOH (1:1) as the bridging/extraction solvent, and then analyzed by nanoESI.

FIG. 11 panel B shows subsequent MS analysis with nanoESI. MS/MS spectra. FIG. 11 panel C shows analysis of 10 ng mL$^{-1}$ methamphetamine in 5 μL urine. FIG. 11 panel D shows analysis of 50 ng mL$^{-1}$ benzoylecgonine in 5 μL urine. FIG. 11 panel E shows impact of the number of SFME cycles on the extraction of the analytes, intensities of the MS/MS product ions monitored for methamphetamine (m/z 150→91), nicotine (m/z 163→130) and benzoylecgonine (m/z 290→168), each at 50 ng/mL in urine samples. 2 kV used for nanoESI.

FIG. 12 panel A shows gently tilting capillary up and down. FIG. 12 panel B shows adding a push-and-pull force by air pressure through a pipette. The pipetting volume was set to 10 μL for this purpose.

FIG. 13 panels A shows 1 ng mL$^{-1}$ verapamil in 5 μL undiluted human pooled blood. FIG. 13 panels B shows the endogenous creatinine contained in human whole blood.

FIG. 14A shows derivations for calculating of concentrations at equilibrium.

FIG. 14B shows derivations for calculating internal standard (IS) incorporation concentrations at equilibrium after SFME.

FIG. 16 panel A shows reactive SFME-nanoESI with a reagent plug injected between the biofluid sample and the extraction solvent. MS/MS spectra of. FIG. 16 panel B shows direct SFME-nanoESI analysis of 200 ng mL-1 epitestosterone in synthetic urine. 5 μL water containing 50 mM hydroxyl amine was used for the reagent liquid plug. FIG. 16 panel C shows reactive SFME-nanoESI analysis of 200 ng mL-1 epitestosterone in synthetic urine. 5 μL water containing 50 mM hydroxyl amine was used for the reagent liquid plug.

FIG. 17 panel B shows progression curve of ATCh digestion determined by SFME-nanoESI. The incubation was over 30 minute and catalyzed by blood cholinesterase (ChE) in room temperature. Acetylthiocholine iodide standard was added into human whole blood with a final concentration of 1.8 mg/mL before incubation. The intensity ratios of product ions from thiocholine (m/z 102→61) and enzyme substrate (m/z 162→103) were monitored using MRM. FIG. 17 panel C shows evaluation of blood ChE with different levels of enzyme inhibition. The ChE activity in blood sample was determined by SFME-nanoESI after 5 min incubation.

FIG. 18 panel B shows investigation of the impact on enzymatic activity by the extraction solvents. For testing of a particular solvent, 5 µL blood sample (diluted) was injected into the capillary with the extraction solvent plug immediately after the mixing the acetylthiocholine into the blood. After the 5 min incubation in capillary, the TCh/ATch ratio was measured using SFME nanoESI MS. For the control, 5 min after the mixing acetylthiocholine into the diluted blood, the sample was taken and analyzed immediately using SFME nanoESI MS with ethyl acetate as the extraction phase. Spray voltage of 1.5 kV was used for nanoESI.

FIG. 20 panel A shows 0.5 ng mL$^{-1}$ methamphetamine in bovine whole blood. FIG. 20 panel B shows 0.5 ng mL$^{-1}$ amitriptyline in bovine whole blood. FIG. 20 panel C shows 0.8 ng mL$^{-1}$ verapamil in bovine whole blood. FIG. 20 panel D shows 9 ng mL$^{-1}$ epitestosterone in synthetic urine using reactive SFME.

FIG. 22 is a table showing LODs obtained with SLME nanoESI and cut-off concentrations for detection or monitoring.

ratio measured with variations in volumes for the extraction solvent with Internal Standard (ethyl acetate containing 40 ng/mL amitraz (IS)) and urine samples containing cotinine as the analyte (A) at 300 ng/mL. Volume of ethyl acetate randomly selected between 6-9 µL.

Figure 26:
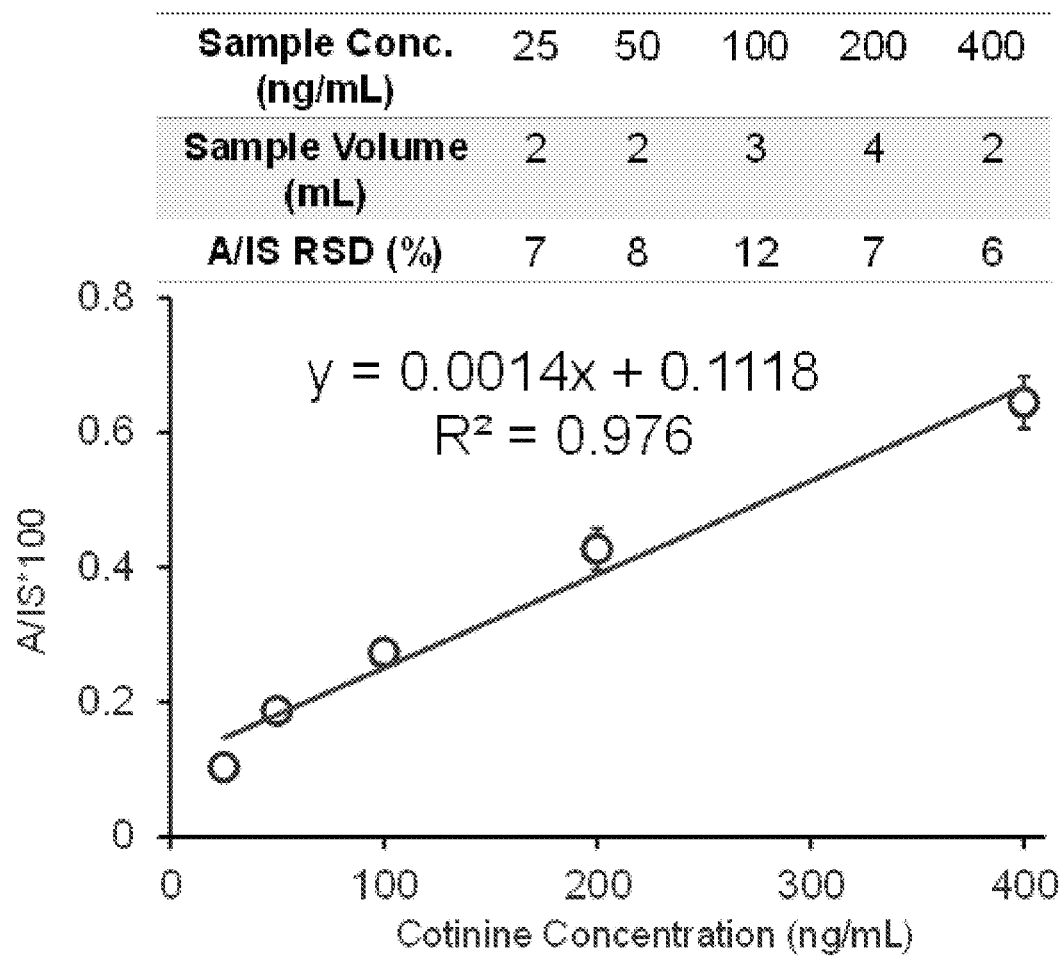

FIG. 26 shows a calibration curve established with $$\frac{I_a}{I_{IS}}$$

ratios measured for a series urine samples of different volumes and continuing cotinine at different concentrations. 10 µL ethyl acetate continuing verapamil (log P=3.8) at 5 ng/mL was used as the extraction solvent for each SFME.

Figure 27A:
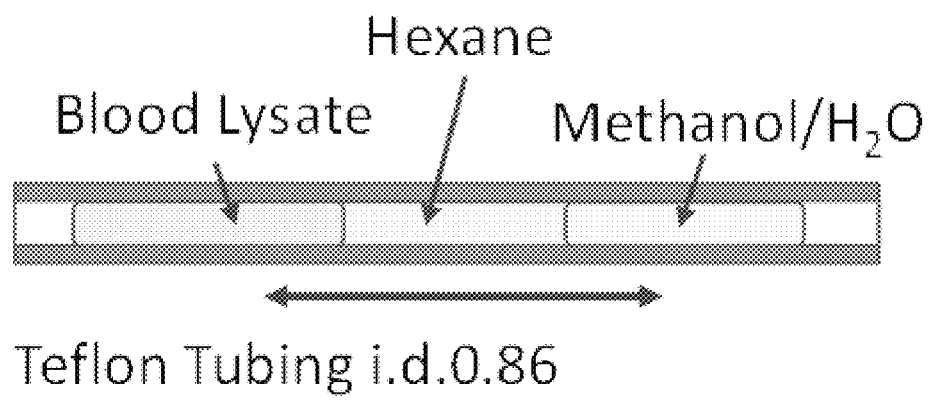
Figure 27B:
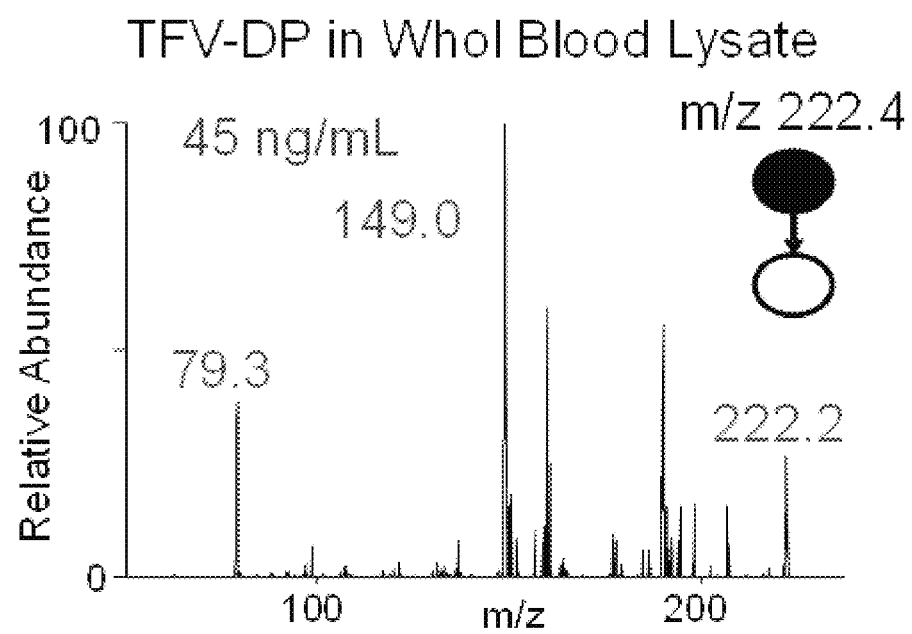

FIG. 27A is a schematic illustrating 3-phase slug flow micro extraction. FIG. 27B is an MS/MS spectrum recorded using TSQ for 45 ng/mL TFV-DP in 10 µL, whole blood lysate.

DETAILED DESCRIPTION

The invention provides systems and methods for slug flow microextraction (SFME), optionally followed by ionization of the extracted analyte for rapid analysis of samples. Systems and methods of the invention are useful for analysis of analytes in any commercial or research field, such as the biomedical field, the pharmaceutical field, the food safety field and environmental fields.

Figure 1A:
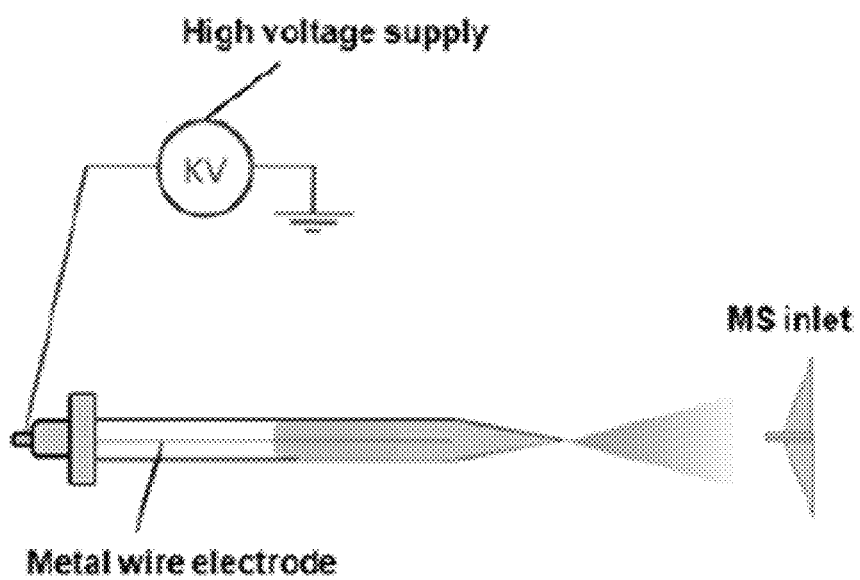
FIG. 1A shows an exemplary system of the invention.

In certain embodiments, the invention provides a system for analyzing an analyte in a sample. FIG. 1A provides an exemplary embodiment of a system of the invention. The system includes an ionization probe and a mass spectrometer. The ionization probe includes a hollow body that includes a distal tip. Numerous different types of hollow bodies can be envisioned by the skilled artisan, and all will work with systems of the invention. The hollow body can have a distal tip for ejecting a spray of a solvent that is loaded into the probe. An exemplary hollow body is a nano-ESI probe capillary with a distal tip. Exemplary nano-ESI probes are described for example in each of Karas et al. (Fresenius J Anal Chem. 366(6-7):669-76, 2000) and El-Faramawy et al. (J Am Soc Mass Spectrom, 16:1702-1707, 2005), the content of each of which is incorporated by reference herein in its entirety. Nano-ESI needles are commercially available from Proxeon Biosystems (Odense, Denmark) and New Objective Inc (Woburn, Mass.). In other embodiments, the system may include a sample cartridge containing one or more spray tips and one or more electrodes.

An exemplary hollow body is a glass borosilicate capillary of 0.86 mm inner diameter with a pulled tip. The tip will typically have a diameter from about 2 µm to about 50 µm. Plastic and rubber tubing can also be used for the hollow body. For example, the hollow body can be composed of PEEK tubing (polyether ether ketone polymer tubing) or TEFLON tubing (polytetrafluoroethylene (PTFE) polymer tubing) or TYGON tubing (flexible tubing consisting of a variety of base materials).

An exemplary hollow body is a fused silica capillary of 0.5 mm or 0.25 mm inner diameter, with or without a pulled tip.

As shown in FIG. 1A, the hollow body is loaded with at least two immiscible fluids, such as a solvent and a sample that is immiscible with the solvent, and an extraction is conducted within hollow body of the probe. Those aspects of the invention will be discussed in greater detail below. In certain embodiments, in order to conduct the extraction within the probe body, the body should be devoid of any other material. For example, there are no substrates (e.g., porous substrates, such as paper substrates), filters, beads, gels, or other substances disposed within the body. Rather, the body remains completely empty of other substances in order to receive the immiscible fluids that will be involved in the extraction.

In certain embodiments, magnetic beads are added into the sample and solvent plugs and an alternating magnetic field is applied to induce the movements of the magnetic beads inside the liquid plugs, thereby to facilitate the turbulents inside each plug for transporting the analytes to and from the liquid-liquid interface.

In certain embodiments, an inner surface of the body is coated to adjust the hydrophobicity of the inner surface of the body. Hydrophobic regions may be coated onto the surface using known techniques, such as by using photolithography, printing methods or plasma treatment. See Martinez et al. (Angew. Chem. Int. Ed. 2007, 46, 1318-1320); Martinez et al. (Proc. Natl Acad. Sci. USA 2008, 105, 19606-19611); Abe et al. (Anal. Chem. 2008, 80, 6928-6934); Bruzewicz et al. (Anal. Chem. 2008, 80, 3387-3392); Martinez et al. (Lab Chip 2008, 8, 2146-2150); and Li et al. (Anal. Chem. 2008, 80, 9131-9134), the content of each of which is incorporated by reference herein in its entirety. In certain embodiments, the body is prepared to have a uniform hydrophobicity. In other embodiments, the body can be prepared to have numerous different regions, each have different hydrophobicity, which can be based on the type of liquid that will fill that region of the body. For example, a region of the body that will receive an oil based sample can be treated to be more hydrophobic than a region of the body that will receive a water and methanol based solvent.

In certain embodiments, the hollow body is configured such that there is no electrode disposed on a surface of the body. Instead, an electrode is at least partially disposed within the hollow body. As shown in FIG. 1A, the electrode can be a metal wire that extends into the hollow body. Any metal typically used for electrodes can be used for the metal electrode. That metal wire is connected to a voltage source, such as a high voltage source. The length of the metal wire shown in FIG. 1A is only exemplary. The metal wire can extend any length into the hollow body. The metal wire can extend to a distal end of the hollow body, as shown in FIG. 1A. Alternatively, the metal wire can be much shorter than shown in FIG. 1A, extending not as far into the body. The amount of solvent added to the hollow body will determine the length of the metal wire, as the wire should extend far enough into the body to interact with the solvent that has been added to the body.

As shown in FIG. 1A, the metal wire may be coaxially disposed within the hollow body, although this is not required. Typically, the metal wire does not touch as the walls of the hollow body, as shown in FIG. 1A. The metal wire electrode and its coupling can be removably or permanently attached to the hollow body. As shown in FIG. 1A, the metal wire electrode and its coupling are removably attached to the hollow body. That allows the proximal end of the hollow body to act as a port for introduction of fluids into the body. In such as embodiment, the metal wire electrode and its coupling is removed from the hollow body, leaving an opening through which fluids are introduced into the body. Once introduced, the metal wire electrode and its coupling are attached to the hollow body, sealing the hollow body.

In other embodiments, the attachment is a permanent attachment and one or more separate fluid ports along the body are used to introduce the fluids to the hollow body. Even if the attachment of the metal wire electrode and its coupling to the hollow body is a removable attachment, the hollow body can still include one or more separate ports along the body to introduce the fluids to the hollow body.

As shown in FIG. 1A, the introduction of high voltage to the liquid within the hollow body ejects the liquid from the distal tip of the hollow body in the form of a spray. An inlet of a mass spectrometer is operably located to receive the liquid ejected from the probe. That distance is typically less than 10 mm, however any distance that allows a signal from the sample to be generated within the mass spectrometer is suitable. That distance can by determined by the skilled artisan by simply adjusting the spacing between the probe and the inlet of the mass spectrometer and monitoring the read-out generated by the mass spectrometer.

In other embodiments, the outside wall of the pulled tip can be coated with metal. The high voltage can be applied through the metal coating for the spray ionization.

Any type of mass spectrometer known in the art can be used with proves of the invention. For example, the mass spectrometer can be a standard bench-top mass spectrometer. In other embodiments, the mass spectrometer is a miniature mass spectrometer. An exemplary miniature mass spectrometer is described, for example in Gao et al. (Z. Anal. Chem. 2006, 78, 5994-6002), the content of which is incorporated by reference herein in its entirety. In comparison with the pumping system used for lab-scale instruments with thousands watts of power, miniature mass spectrometers generally have smaller pumping systems, such as a 18 W pumping system with only a 5 L/min (0.3 m3/hr) diaphragm pump and a 11 L/s turbo pump for the system described in Gao et al. Other exemplary miniature mass spectrometers are described for example in Gao et al. (Anal. Chem., 80:7198-7205, 2008), Hou et al. (Anal. Chem., 83:1857-1861, 2011), and Sokol et al. (Int. J. Mass Spectrom., 2011, 306, 187-195), the content of each of which is incorporated herein by reference in its entirety. Miniature mass spectrometers are also described, for example in Xu et al. (JALA, 2010, 15, 433-439); Ouyang et al. (Anal. Chem., 2009, 81, 2421-2425); Ouyang et al. (Ann. Rev. Anal. Chem., 2009, 2, 187-214); Sanders et al. (Euro. J. Mass Spectrom., 2009, 16, 11-20); Gao et al. (Anal. Chem., 2006, 78(17), 5994-6002); Mulligan et al. (Chem.Com., 2006, 1709-1711); and Fico et al. (Anal. Chem., 2007, 79, 8076-8082), the content of each of which is incorporated herein by reference in its entirety.

In certain embodiments, the mass spectrometer inlet is located remote from the ionization probe and an ion transfer member is used to transfer over longer distances. Exemplary ion transfer members are described for example in Ouyang et al. (U.S. Pat. No. 8,410,431), the content of which is incorporated by reference herein in its entirety.

In certain embodiments, the ionization probes of the invention operate without pneumatic assistance. That is, with probes of the invention, pneumatic assistance is not required to transport an analyte; rather, a voltage is simply applied to the substrate that is held in front of a mass spectrometer. However, in certain embodiments, nebulizing gas may be used with systems of the invention to assist with desolvation. The nebulizing gas may either be pulsed or provided as a continuous flow. In other embodiments, a gas generating device is operably coupled to the probe such that it can inject a gas into the hollow body to push the sample and solvent to a distal tip of the probe. The gas will typically be an inert gas, such as nitrogen or argon, but can also be air.

In certain embodiments, the ionization probe is kept discrete (i.e., separate or disconnected) from a flow of solvent, such as a continuous flow of solvent. Instead, discrete amounts of solvent and sample are introduced into the hollow body of the probe. The probe is then connected to a voltage source to produce ions of the sample which are subsequently mass analyzed. The sample is transported through the hollow body without the need of a separate solvent flow. As previously mentioned, pneumatic assistance is not required to transport the analyte; rather, a voltage is simply applied to the solvent in the probe that includes the extracted analyte that is held in front of a mass spectrometer.

Figure 1B:
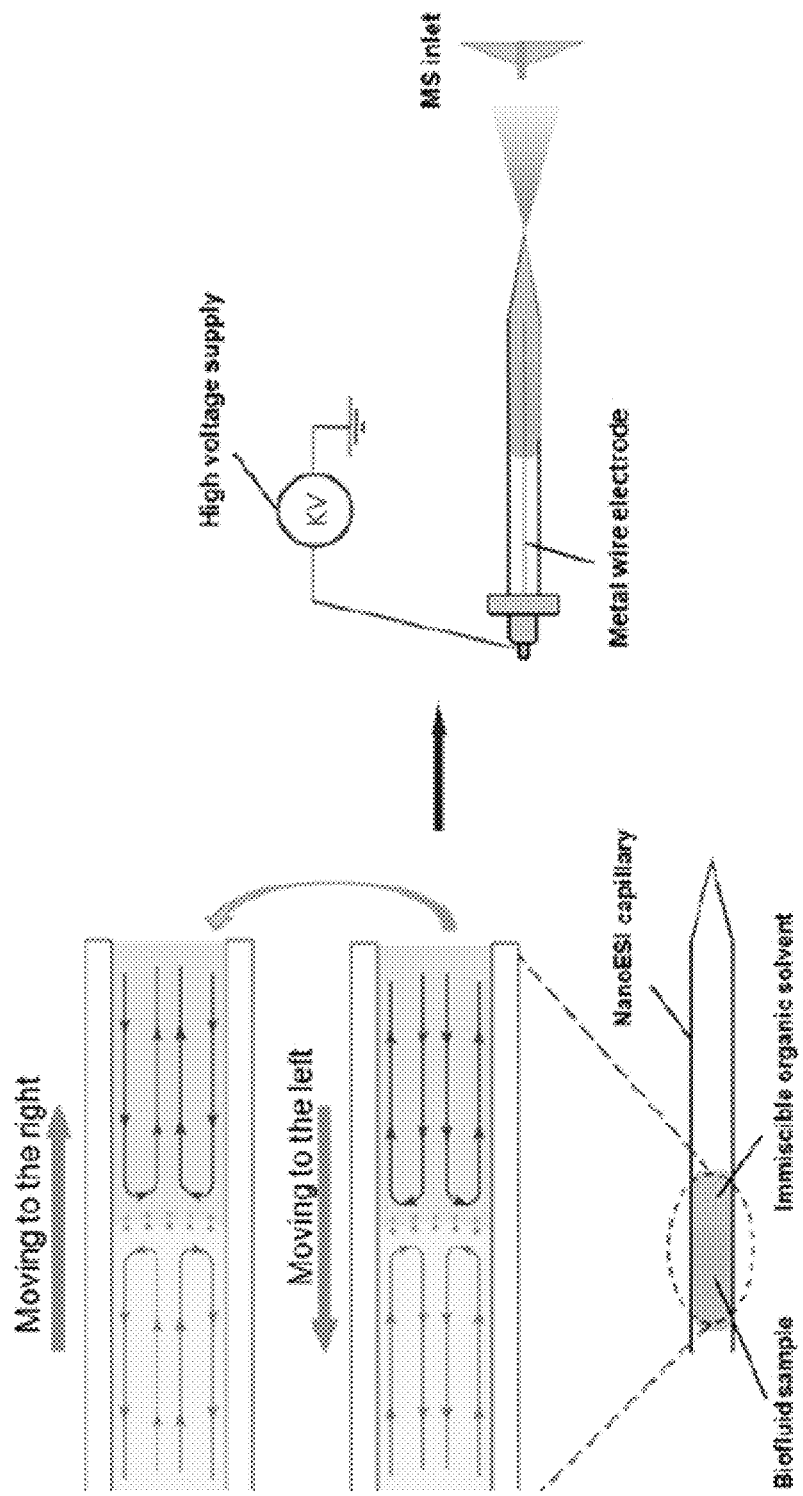
FIG. 1B shows a method of using systems of the invention. In this figure, two immiscible phases, the liquid sample and the organic solvent are injected adjacently in a capillary with a pulled tip. The liquid phases are moved back and forth in the capillary, by tilting the capillary or applying gas pressure, to facilitate the microextraction. The liquid phases are then pushed with the extraction phase reaching the pulled tip of the capillary, by applying a gas pressure, and a wire electrode is inserted into the extraction solvent to apply a DC voltage for nanoESI.

FIG. 1B shows an exemplary method of use for systems of the invention. In certain embodiments, such methods involve introducing a solvent into a hollow body including a distal tip. A sample is also introduced into the hollow body. The solvent is immiscible with the sample and extracts at least one analyte from the sample into the solvent. A voltage is applied to the solvent including the extracted analyte in the hollow body so that the analyte is expelled from the distal tip of the body, thereby generating ions of the analyte. Those expelled ions are then analyzed.

FIG. 1B shows two immiscible phases, the liquid sample and the organic solvent, injected adjacently in a capillary with a pulled tip. Given the different polarity of the different phases, one or more analytes will move from the sample into the solvent (extraction of analytes from the sample into the solvent). That extraction process can be facilitated by causing the liquid phases to move back and forth in the capillary, such as by tilting the capillary or applying gas pressure, to facilitate the microextraction. The liquid phases may then be pushed with the extraction phase reaching the pulled tip of the capillary, by applying a gas pressure (from a gas generating device operably coupled to the probe), and a wire electrode is inserted into the extraction solvent to apply a DC voltage for nanoESI. The voltage causes the solvent to be expelled from the distal tip of the hollow body as a spray which reaches the inlet of the mass spectrometer.

Methods of the invention can be used with any type of sample, such as organic or non-organic, biological or non-biological, etc. In certain embodiments, the sample is derived from a biological tissue or is a biological fluid, such as blood, urine, saliva, or spinal cord fluid. The sample may include an analyte of interest to be analyzed. That analyte can be native to the sample or may have been introduced into the sample. Exemplary analytes include therapeutic drugs, drugs of abuse and other biomarkers. The Examples herein show that effective suppression of the matrix effect was achieved for therapeutic drugs, drugs of abuse and other biomarkers. In certain embodiments, systems and methods of the invention can be used for direct analysis of the biofluid samples or liquid samples.

Figure 19:
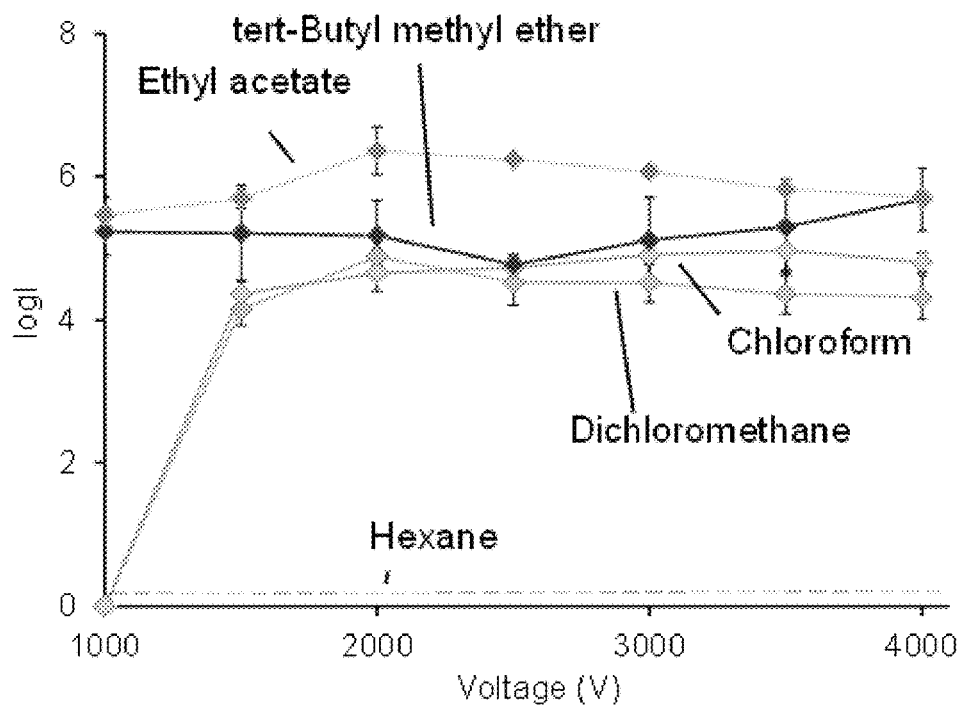
FIG. 19 shows comparison of different organic solvents for extraction phase used in SFME-nanoESI. For each test, the whole bovine blood spiked with 5 ng mL$^{-1}$ methamphetamine was diluted 10 times with water; 5 µL sample was then used to prepare the sample plug and 5 µL of one organic solvent was used for the extraction plug. SRM (single reaction monitoring) with a transition m/z 150→91 was used to record the intensity of product ion m/z 91 from protonated methamphetamine m/z 150, while the spray voltage is varied.

The solvent may be any solvent so long as it is immiscible with the sample and works for both extraction and ionization of the sample. Typically, the chosen solvent will depend on the sample to be analyzed and/or the analyte of interest believed to be in the sample (FIG. 19). A factor to be considered is the polarity of the solvent. In the 2-phase extraction system, ideally the solvent has a different polarity then the sample and/or the analyte of interest believed to be in the sample. For example, an aqueous sample will typically have a high polarity, and therefore a good choice of solvent would be an organic solvent with a low polarity (e.g., methanol or ethyl acetate or mixtures that include those solvents e.g., water/methanol mixtures or water/ethyl acetate mixtures). An oil sample will typically have a low polarity, and therefore a good choice of solvent would be a solvent with a higher polarity, such as a water/methanol mixture. The skilled artisan will be able to determine the proper solvent to use based on the sample to be analyzed.

Another consideration of the solvent is that in addition to being good for an extraction of an analyte from a sample, it can also be used to ionize the sample. That is, the solvent can be compatible for both the extraction and the ionization of the extracted analyte. As illustrated in the Example, methanol and ethyl acetate work well for extraction of analytes as well as for ionization of analytes, while chloroform works well for extraction but not for ionization of analytes. Typically, a solvent that is compatible with electrospray ionization can possibly be used with systems and methods of the invention, so long that solvent is also immiscible with the sample and is able to extract an analyte from the sample. The skilled artisan having experience in mass spectrometry will know particular solvents that are compatible with electrospray ionization.

Methods of the invention can also involve real-time chemical reactions that can be used for improving the overall analysis efficiency of the target analytes. To perform such a derivation, a solution containing an agent that imparts a charged function group to the analyte is introduced to the hollow body. That solution is typically introduced between the solvent and the sample. The agent in the solution interacts with the analytes in the sample and imparts a charged functional group to the sample, allowing for the ionization of the analyte.

In certain embodiments, more than one analyte (e.g., a plurality of analytes) is extracted from the sample and into the solvent. The plurality of analytes can be extracted at the same time. Alternatively, the analytes are differentially extracted into the solvent, typically based on the polarity of the analyte and the polarity of the solvent.

Figure 6:
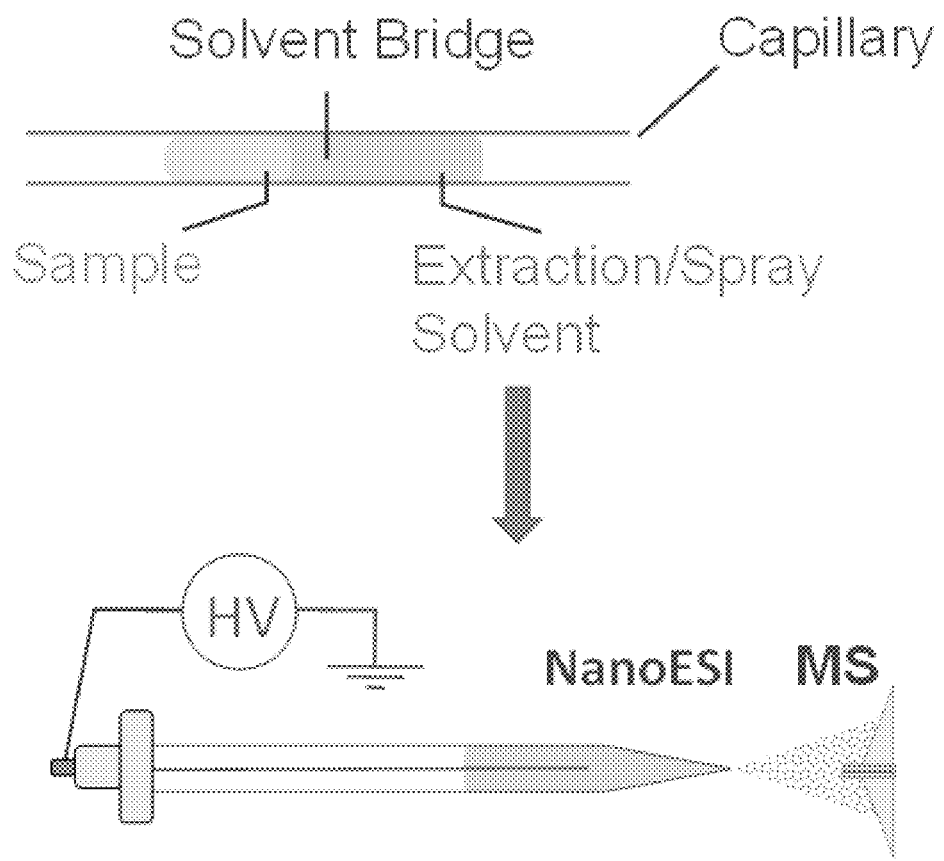
FIG. 6 shows an exemplary three-phase fluid system. Sample analysis using immiscible three phase SFME: Sample phase is of high polarity and the solvent of relatively high polarity, such as $H_2O$ and acetonitrile, is used as extraction solvent. Solvent of relatively low polarity which is immiscible with sample and extraction solvent is plugged between them and keep them separated. A hydrophobic tubing rather than a glass tubing is used in this case to ensure the isolation. A push and pull force is applied to induce the slug flow movement for extraction. After the extraction, the extract can be either directly or indirectly analyzed by nanoESI, or stored for further operations.

While methods of the invention have been discussed using two immiscible fluid, the systems and methods of the invention are not limited to the use of two fluids. Any number of fluids can be used with systems and methods of the invention, such as three fluids, four fluids, five fluids, etc. In certain embodiments, a three fluid system is used. In such embodiments, two miscible fluids are separated by an immiscible fluid. An exemplary three fluid system is shown in FIG. 6. The polarities of the Sample-Solvent Bridge-Extraction/Spray Solvent can be high-low-high or low-high-low. A capillary surface with proper hydrophobicity can be selected to stabilize the solvent bridge, which separates the sample phase and the extraction solvent phase of similar polarities (which means they are miscible). As an example, a urine sample plug and a methanol/water plug for extraction can be separated by ethyl acetate or hexane, and a Teflon capillary with hydrophobic surface can be used.

In certain embodiments, systems and methods of the invention can also be used for preparing samples that will be analyzed later. The extraction solvent can be stored as the liquid sample or deposited on paper substrate or MALDI plate to prepare the dried sample spots. The internal standard can be incorporated in to the dried sample spots during the SFME process. The target analytes can be chemical modified during the SFME process.

In other embodiments, the hollow body does not require a distal tip because the extraction capillary is not used as an ionization probe. In such embodiments, the extraction is simply conducted as described above in a capillary. After the extraction is completed, the solvent containing the extracted analyte is removed from the capillary and is then analyzed using any method known in the art. For example, the solvent containing the extracted analyte may be loaded into a separate ionization probe and then analyzed by mass spectrometry, such as shown in FIG. 6. In other embodiments, the analyte is analyzed in a different manner, such as any spectroscopy technique or other assay known in the art.

In other embodiments, the invention provides methods that are analyzing larger volume samples. Larger volume samples are samples greater than 100 μl, as opposed to small volume samples, which are samples less than 100 μl. Exemplary large volume samples can range from the microliter range (e.g., greater than 100 μl) into the milliliter range, and into the liter range and above.

Typically, larger volume samples are contained in a vessel, such as a standard vessel for holding a biological sample, such as a VACUTAINER (blood collection tube, commercially available from BD). Other vessels, such as standard laboratory vessels (beakers, flasks, etc.) can be used to hold larger volume samples.

Larger volume samples typically include urine samples or other biological fluids, such as blood. Generally, a body fluid refers to a liquid material derived from, for example, a human or other mammal. Such body fluids include, but are not limited to, mucus, blood, plasma, serum, serum derivatives, bile, phlegm, saliva, sweat, amniotic fluid, mammary fluid, urine, sputum, and cerebrospinal fluid (CSF), such as lumbar or ventricular CSF. A body fluid may also be a fine needle aspirate. A body fluid also may be media containing cells or biological material. Larger volume samples can also be environmental samples, such as river water, soil, etc.

In addition to native components of the sample, the biological or environmental samples can include a non-native biological agent that can be analyzed by methods of the invention. Exemplary environmental samples include a water sample or a soil sample. In certain embodiments, a biological agent include all genuses and species of bacteria and fungi, including, for example, all spherical, rod-shaped and spiral bacteria. Exemplary bacteria are stapylococci (e.g., *Staphylococcus epidermidis* and *Staphylococcus aureus*), *Enterrococcus faecalis*, *Pseudomonas aeruginosa*, *Escherichia coli*, other gram-positive bacteria, and gram-negative *bacilli*. An exemplary fungus is *Candida albicans*. A biological agent also includes toxins secreted by bacteria or fungi. For example, *E. coli* secretes Shiga-like toxin (Zhao et al., Antimicrobial Agents and Chemotherapy, 1522-1528, 2002) and *C. Difficile* secretes Exotoxin B (Sifferta et al. Microbes & Infection, 1159-1162, 1999). A biological agent can also include an allergen. An allergen is a non-parasitic antigen capable of stimulating an immune response in a subject. Allergens can include plant pollen or dust mite excretion.

The extraction solvent may be suitable for extracting nucleic acid from the biological agent. SDS-based extraction may be suitable. See for example, Bhat et al. (U.S. Pat. No. 7,208,654), the contents of which are incorporated by reference herein in their entirety.

Incorporation by Reference

References and citations to other documents, such as patents, patent applications, patent publications, journals, books, papers, web contents, have been made throughout this disclosure. All such documents are hereby incorporated herein by reference in their entirety for all purposes.

Equivalents

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLES

Example 1

Micro-Extraction Protocol

Figure 2:
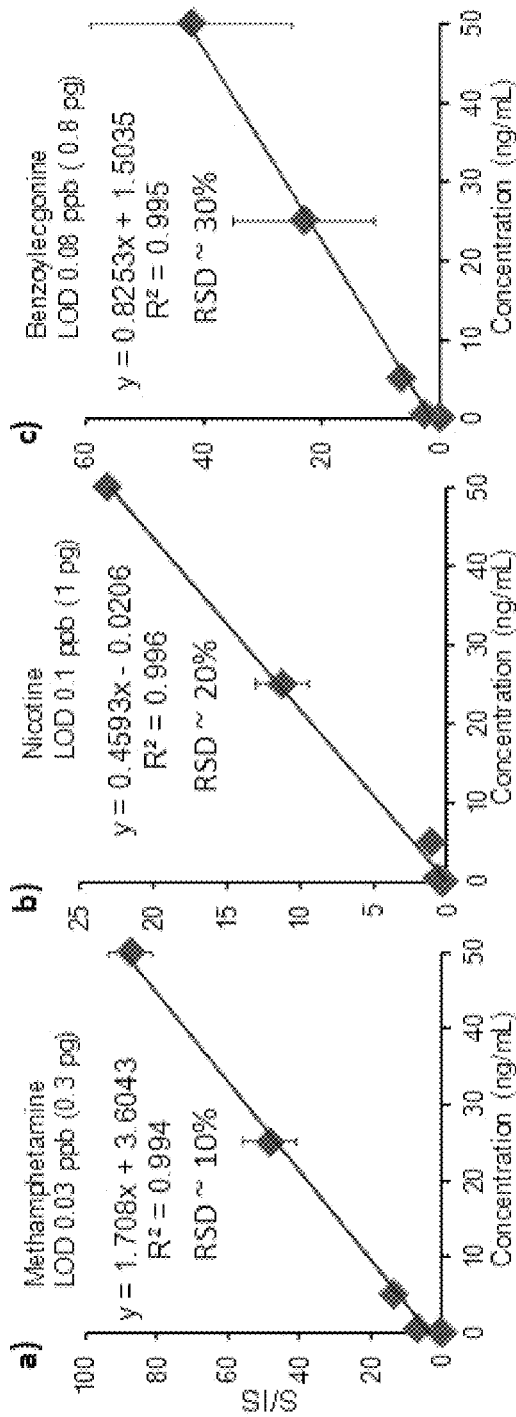
FIG. 2 panels A-C show calibration curves for quantitation of different compounds in synthetic urine samples.

Systems and methods of the invention were used to analyze 10 μL urine samples containing benzoylecgonine, nicotine or methamphetamine, with LODs better than 1 ng/mL achieved (FIG. 2 panels A-C). Chemical equilibrium was reached faster at higher tilting rates (~30/minute). Significant improvement of signal was observed even for analytes with relatively low patrician coefficient for the extraction solvent, due to an effective suppression of the matrix effect. Different solvents were tested for the extraction. Nonpolar solvents such as chloroform were found to be efficient for extraction but relatively poor for subsequent ionization. An on-line injection of methanol could be used to facilitate the direct ionization of the analytes extracted into these solvents. Ethyl acetate, however, was found to be effective for both extraction and ionization, such as by nanoESI. Various methods have also been explored for incorporation of internal standards for quantitation while maintaining the operation procedure simple. A calibration of nicotine with good linearity (R2=0.99) has been obtained (FIG. 2 panel B).

Example 2

Real-Time Derivatization

Figure 3A:
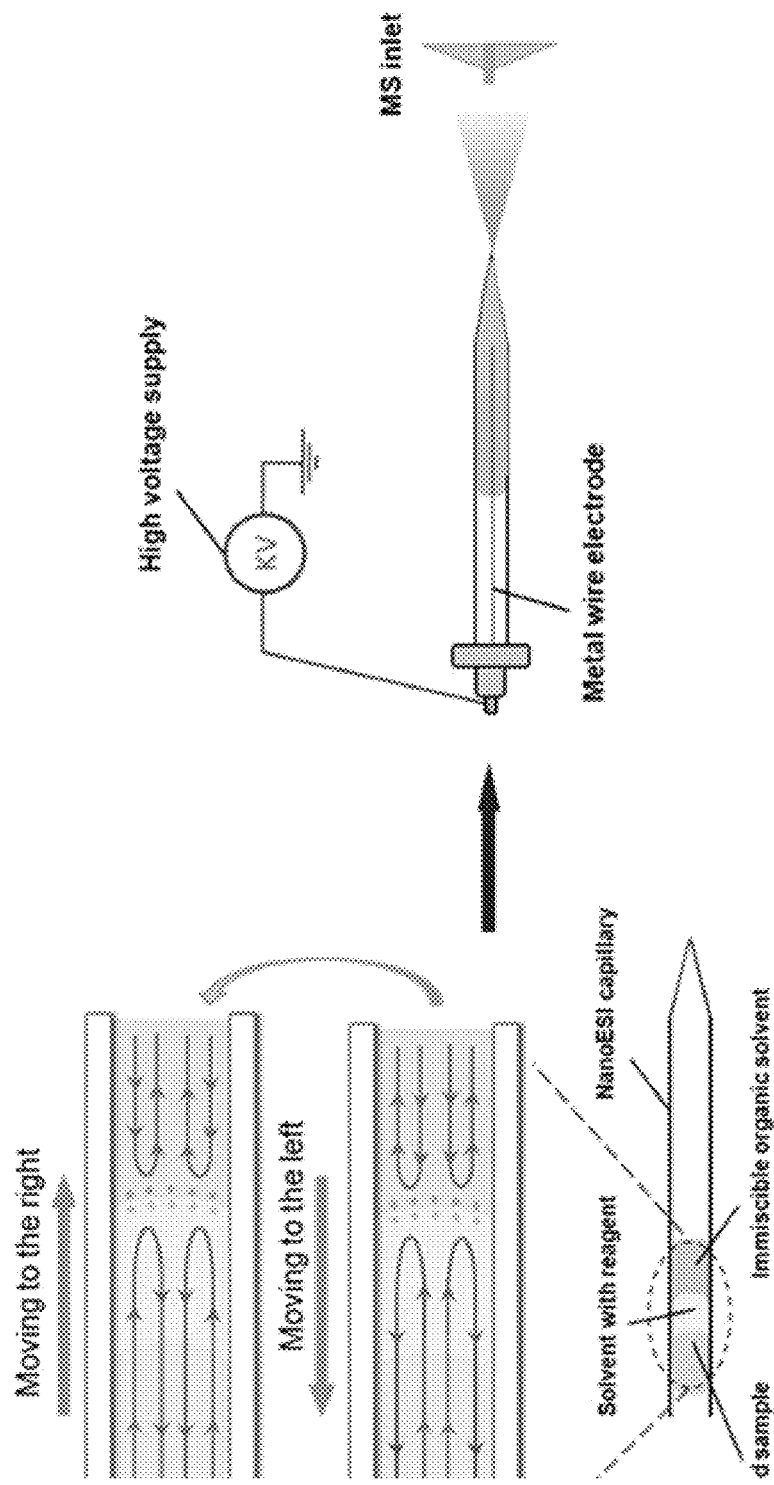
FIG. 3A shows reactive slug flow microextraction nanoESI with a sample phase, a derivatization reagent phase and an extraction phase injected adjacently. The extraction phase is immiscible with the reagent phase or the sample phase; the sample phase and the reagent phase can be miscible. The analytes in the sample phase are derivatized and extracted into the extraction phase during the SFME operation. The liquid phases are then pushed so the extraction phase reaches the pulled tip of the capillary and a wire electrode is inserted into the extraction phase to apply the DC spray voltage for nanoESI.
Figure 3B:
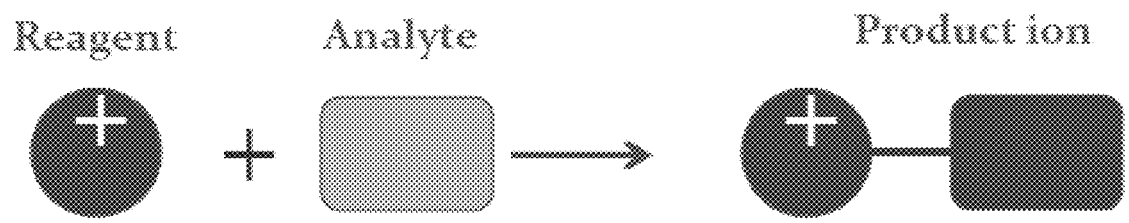
FIG. 3B shows the binding of a charged reagent to a target in a sample to form a charged complex, which is more amenable to spray ionization than the uncharged target.

Methods of the invention can also involve real-time chemical reactions that can be used for improving the overall analysis efficiency of the target analytes. This is exemplified by the analysis of a steroid in urine. The efficiency was expected to be high for extracting steroids from the urine; however, steroids are difficult to ionize by spray ionization. A real-time derivatization was performed for SFME-nanoESI by injecting 3 μL aqueous solution with 5% hydroxylamine between the extraction solvent (ethyl acetate) and the urine sample (FIGS. 3A-B). The reactant solution mixed quickly with the sample and the steroids were derivatized with a charged function group while being extracted into the organic phase. The signals in MS spectra were improved by multiple orders of magnitudes. LODs of 0.2, 0.7, 0.6, 0.8 ng/mL were obtained for 5α-androstan-3β, 17β-diol-16-one, epitestosterone, 4,6-cholestadien-3-one, and stigmastadienone, respectively, in urine samples of amounts below 10 mL.

Reaction Scheme

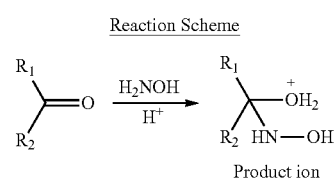

Product ion

Scheme 1. Reaction between hydroxylamine and the carbonyl groups on steroids

Figure 5:
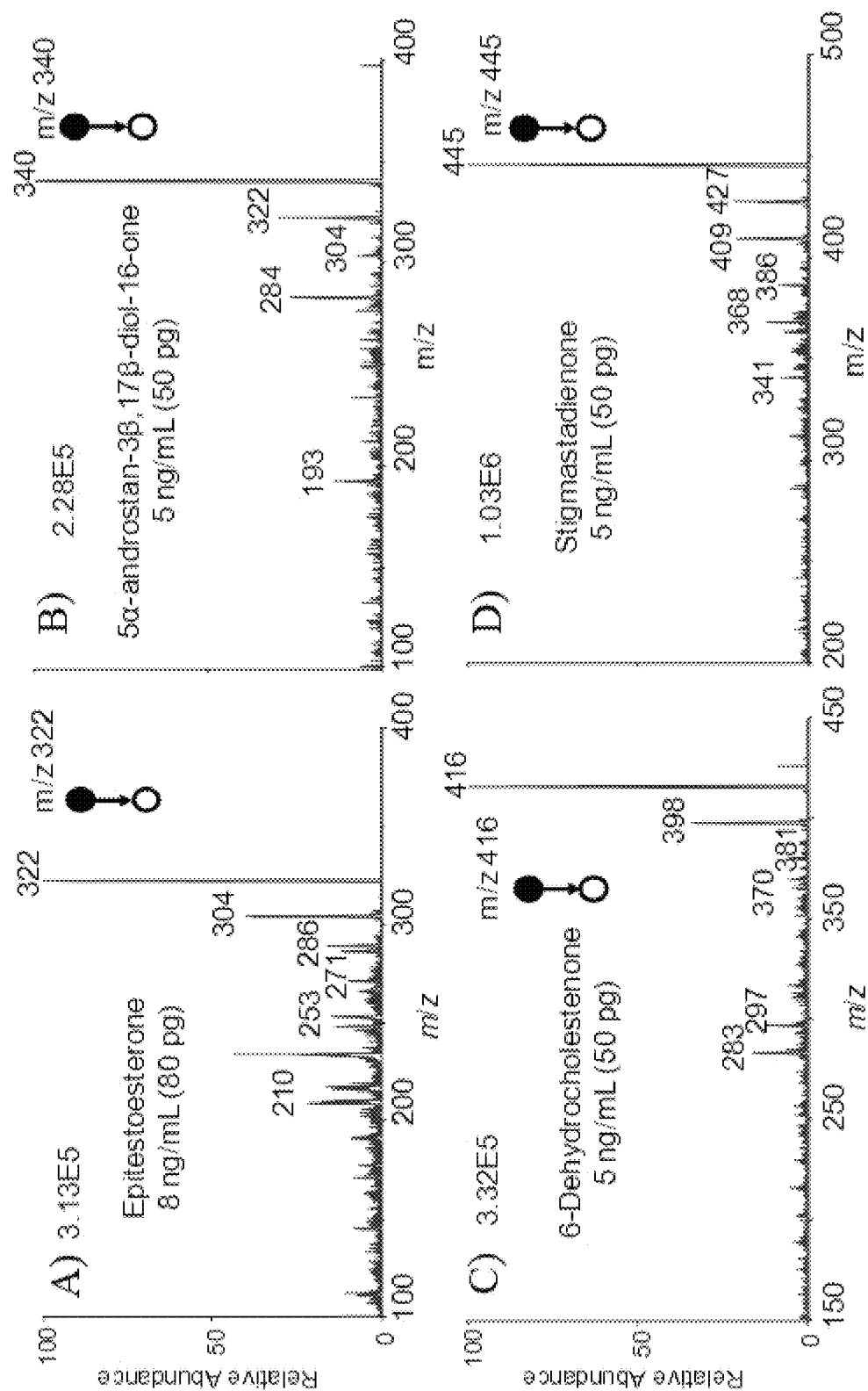
FIG. 5 panels A-D show MS/MS spectra obtained using reactive slug flow microextraction nanoESI with hydroxylamine as the reagent. 10 μL of 8 ng/mL epitestosterone (FIG. 5 panel A), 5 ng/mL 5α-androstan-3β, 17β-diol-16-one (FIG. 5 panel B), 5 ng/mL 6-dehydrocholestenone (FIG. 5 panel C), and 5 ng/mL stigmastadienone (FIG. 5 panel D) in synthetic urine. 5 μL aqueous solution containing 0.1% acetic acid and 10% hydroxylamine were added as the reagent phase. 5 μL ethyl acetate was used as the extraction phase.

FIG. 5 panels A-D show MS/MS spectra obtained using reactive slug flow microextraction nanoESI with hydroxylamine as the reagent. 10 µL of 8 ng/mL epitestosterone (FIG. 5 panel A), 5 ng/mL 5α-androstan-3β, 17β-diol-16-one (FIG. 5 panel B), 5 ng/mL 6-dehydrocholestenone (FIG. 5 panel C), and 5 ng/mL stigmastadienone (FIG. 5 panel D) in synthetic urine. 5 µL aqueous solution containing 0.1% acetic acid and 10% hydroxylamine were added as the reagent phase. 5 µL ethyl acetate was used as the extraction phase.

The analysis of the samples described above would otherwise need to be analyzed using traditional lab procedures using sample extraction, liquid chromatography, and mass analysis using electrospray ionization or atmospheric pressure chemical ionization. The sample amounts required are significantly larger (~1 mL).

Example 3

Direct Analysis of Biological Fluids with Low Viscosity

Biological samples such as urine were directly analyzed using the SFME nanoESI. FIG. 2 panels A-C. Calibration curves for quantitation of methamphetamine (FIG. 2 panel A), nicotine (FIG. 2 panel B), and benzoylecgonine (FIG. 2 panel C) in synthetic urine samples. 10 µL synthetic urine containing the drugs and internal standards were used as samples for the measurement. 5 µL ethyl acetate (EA) was used as the extraction phase for extraction, purification and spray. Internal standards: methamphetamine-d8 at 0.8 ng/mL, nicotine-d32 at ng/mL, benzoylecgonine-d3 at 1 ng/mL. The single reaction monitoring (SRM) transitions used: methamphetamine m/z 150→91, methamphetamine-d8 m/z 158→93; nicotine 163→130, nicotine-d3 m/z 166→130; benzoylecgonine m/z 290→168, benzoylecgonine-d3 m/z 293→171. Partition coefficients: $LogP_{methamphetamine}=2.07$; $LogP_{nicotine}=1.17$, $LogP_{benzoylecgonine}=-0.59$.

The matrix effect due to high concentration salts were minimized. Good LODs were obtained for drugs of abuse, even for benzoyecgonine with relatively low partition coefficient for the extraction phase. The partition coefficient (LogP) is defined as: $LogP=log([solute]_{octanol}/[solute]_{water})$, which represents the differential solubility of an un-ionized compound in an organic phase such as octanol immiscible with the aqueous phase at equilibrium.

Example 4

Direct Analysis of Viscous Biofluids

Figure 4:
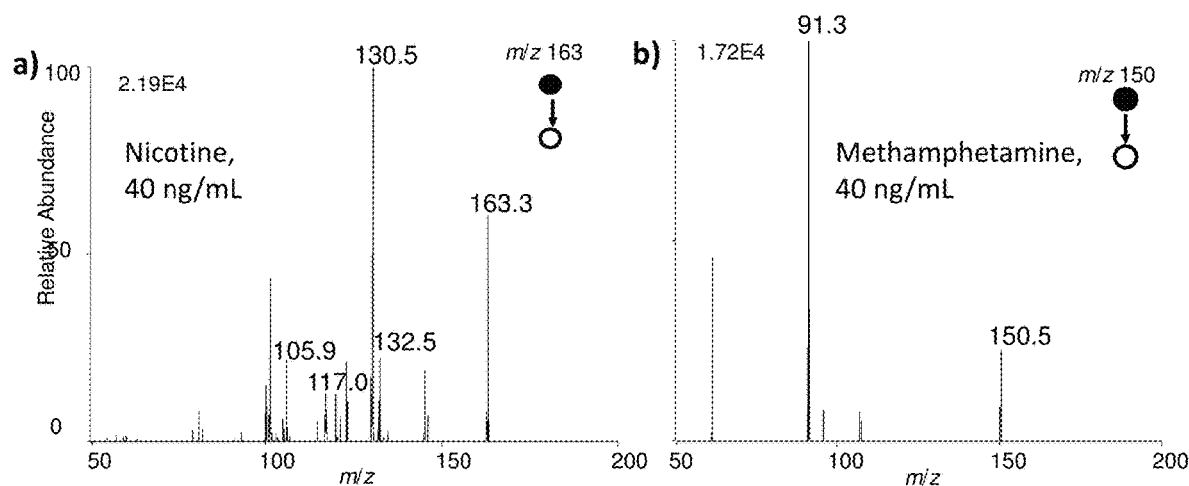
FIG. 4 panels A-B show MS/MS spectra obtained using slug flow microextraction nanoESI. Bovine blood samples, each containing 40 ng/mL nicotine (FIG. 4 panel A) and 40 ng/mL methamphetamine (FIG. 4 panel B) were diluted 10 times with water and then analyzed using SFME nanoESI. 10 μL of diluted sample, 5 μL ethyl acetate used.

For viscous biofluid samples, dilution of the sample was applied to allow the operation with systems and methods of the invention. As an example, blood samples containing drugs were diluted 10 times before analysis by SFME nanoESI. The data in FIG. 4 panels A-B show that methods of the invention were able to analyze analytes from a blood sample. FIG. 4 panels A-B show MS/MS spectra obtained using slug flow microextraction nanoESI. Bovine blood samples, each containing 40 ng/mL nicotine (FIG. 4 panel A) and 40 ng/mL methamphetamine (FIG. 4 panel B) were diluted 10 times with water and then analyzed using SFME nanoESI. 10 µL of diluted sample, 5 µL ethyl acetate used.

Example 5

Summary of the Analytical Performance

TABLE 1

Limits of detection of chemicals in synthetic urine and blood samples achieved using slug flow microextraction nanoESI

| Compound | Matrix | Derivatization | Sample volume (µL) | LOD (ng/mL) |
| --- | --- | --- | --- | --- |
| Methamphetamine | Synthetic urine | NA | 5 | 0.03 |
|  | Bovine blood | NA | 5 | <40 |
| Nicotine | Synthetic urine | NA | 5 | 0.1 |
|  | Bovine blood | NA | 5 | <40 |
| Benzoylecgonine | Synthetic urine | NA | 5 | 0.08 |
| Epitestosterone | Synthetic urine | hydroxylamine | 5 | 0.7 |
| 6-dehydro-cholestenone | Synthetic urine | hydroxylamine | 5 | 0.6 |
| 5α-androstan-3β,17β-diol-16-one | Synthetic urine | hydroxylamine | 5 | 0.2 |
| Stigmastadienone | Synthetic urine | hydroxylamine | 5 | 0.8 |

Example 6

Direct Analysis of Oil Samples

Figure 7:
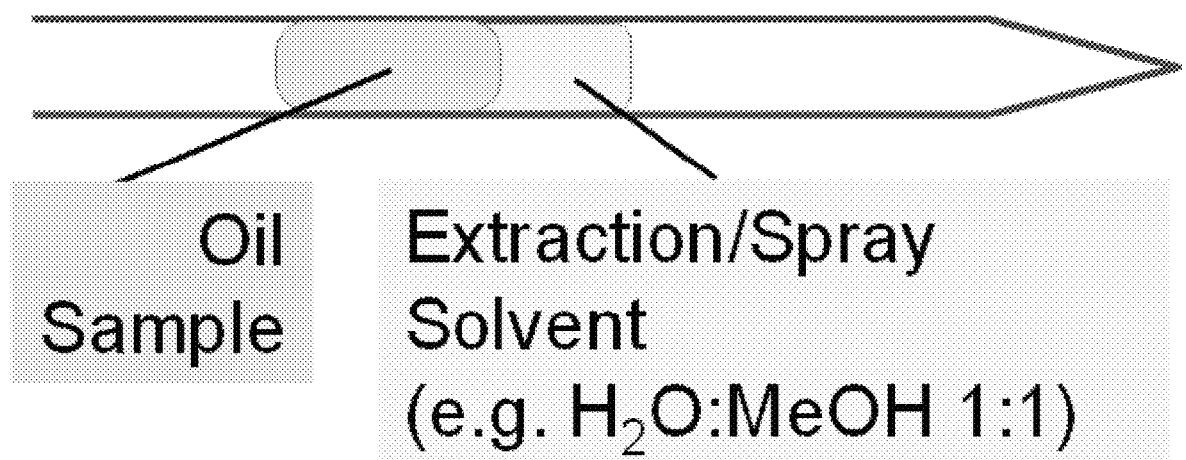
FIG. 7 shows microextraction for analyzing chemicals in low-polarity samples. Solvents of relatively high polarity can be used for extraction and spray ionization.

The Examples above show that the drug compounds in aqueous samples of high polarities, such as blood or urine, were extracted to organic solvents of low polarity. The systems and methods of the invention can also be applied by extracting analytes from samples of low polarity samples, such as oil, to the extraction solvent of high polarity, such as the water/methanol solvent as shown in FIG. 7. The results are shown in FIG. 8, which shows analysis of vegetable oil using systems and methods of the invention. A mixture of water and methanol was used as the extraction solvent. FIG. 8 panel A is an MS spectrum showing that diacylglycerol and triacylglycerol species were observed in the MS spectrum in positive mode. FIG. 8 panel B is an MS spectrum showing that different fatty acids were observed in the MS spectrum acquired in negative mode.

Example 7

Three-Phase Methods

Figure 9:
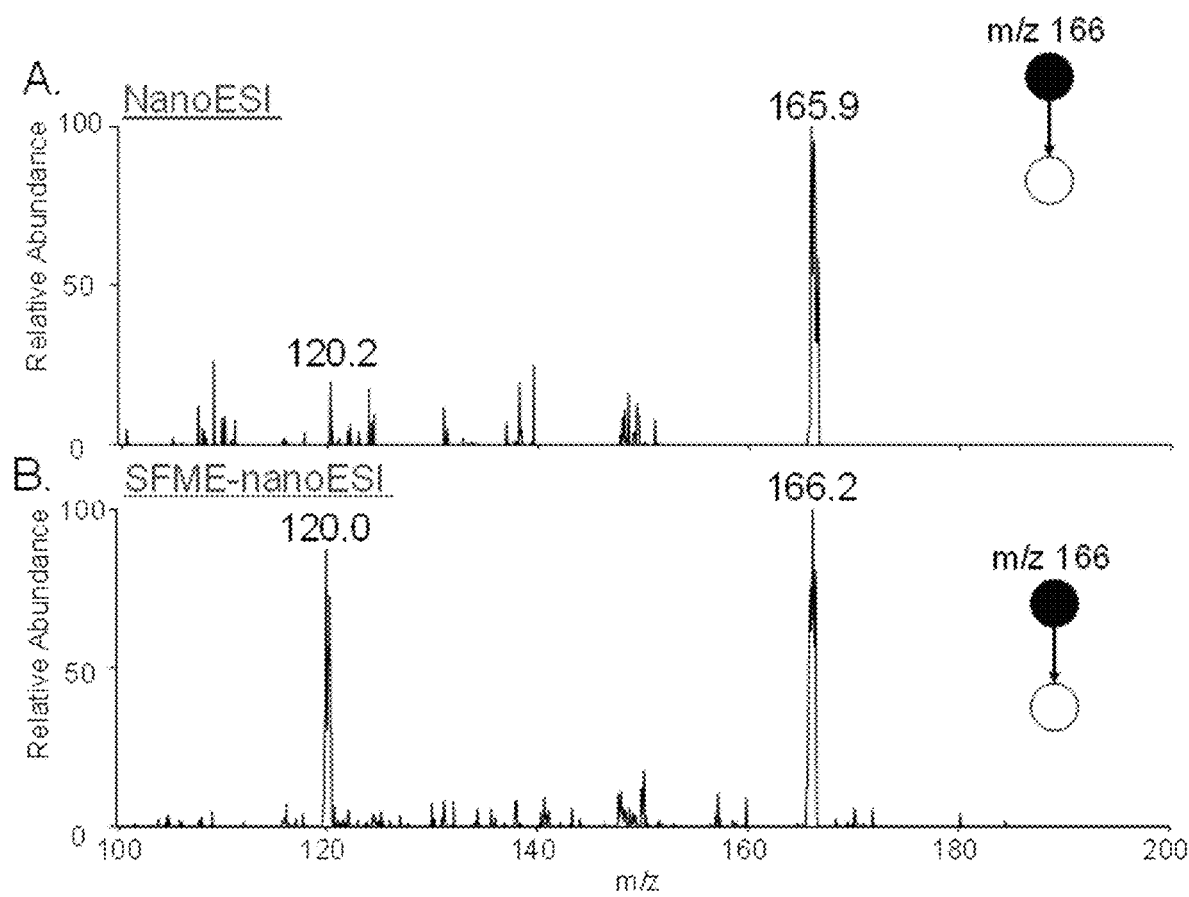
FIG. 9 panels A-B show analysis of 100 ng/mL phenylalanine (165 Da, logP=−1.38) in urine using the 3-phase SFME (FIG. 6). MS/MS spectrum of the molecular ion were collected.

A three-phase method can be performed as exemplified in FIG. 6. The polarities of the Sample-Solvent Bridge-Extraction/Spray Solvent can be high-low-high or low-high-low. A capillary surface with proper hydrophobicity can be selected to stabilize the solvent bridge (middle phase), which separates the sample phase and the extraction solvent phase of similar polarities (which means they are miscible). As an example, the urine sample plug and the methanol/water plug for extraction can be separated by ethyl acetate or hexane, and a Teflon capillary with hydrophobic surface can be used. Analysis of phenylalanine from urine is shown in FIG. 9 panels A-B. Phenylalanine is of relatively high polarity. The phenylalanine molecules were extracted from the urine to $H_2O$:MeOH (1:1) through the hexane, which separates them from the salts in the urine. This is a purification process.

If two-phase methods with urine and hexane are used, phenylalanine is of relatively high polarity so the solubility in hexane is relatively low and the concentration would be low in hexane. Also, hexane is much less favorable for spray ionization in comparison with the polar solvents such as $H_2O$:MeOH (1:1). The three-phase methods with a sample-bridge-spray in an polarity order as high-low-high allow a compound of high polarity to be concentrated into a high polarity solvent, which is suitable for spray ionization. The subsequent analysis is done by transferring the extraction solvent to a capillary with a pulled tip for spray ionization (FIG. 6) or with a direct spray ionization from the capillary as previously described above.

Real time chemical derivatization can be applied by adding the reaction reagents in either or both of the bridge solvent or the extraction/spray solvent. Real time internal standard incorporation can be applied by pre-adding the internal standards in either of both of the bridge solvent of the extraction/spray solvent.

Example 8

Micro-Extraction in a Fused Silica Tubing (i.d. 500 μm)

The SFME sample processing can be done in fused silica tubing of smaller diameter which are commonly used as liquid line in liquid chromatography system (e.g., tubing having an inner diameter of 500 μm or less). The extraction can be induced by applying a push and pull force on one side of the tubing. The extract can be either directly analyzed by nanoESI or stored for further operations.

Figure 10:
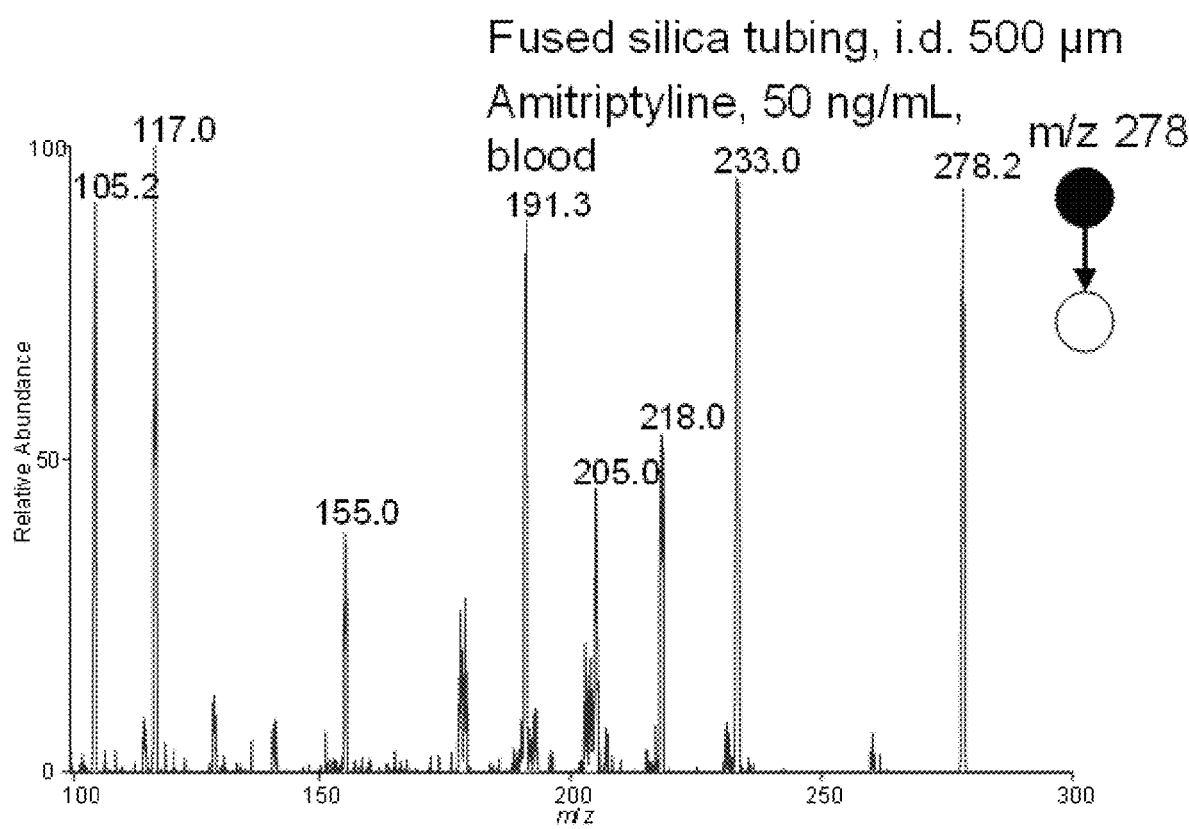
FIG. 10 show analysis of 50 ng/mL amitriptyline in bovine whole blood using a fused silica capillary.

FIG. 10 show analysis of 50 ng/mL amitriptyline in bovine whole blood. MS/MS spectrum of the molecular ion was collected. The blood sample was first 10× diluted using $H_2O$ as a reduction of viscosity. For extraction, 5 μL of the diluted sample was processed in a fused silica tubing (i.d. 500 μm) using methods of the invention. The extract was then infused into a nanoESI emitter and analyzed by nanoESI.

Example 9

Direct Mass Spectrometry Analysis of Biofluid Samples Using Slug Flow Microextraction NanoESI Direct mass spectrometry (MS) analysis of biofluids with simple procedures represents a key step in translation of MS technologies to the clinical and point-of-care applications. The current study reports the development of a single-step method using slug flow microextraction and nanoESI (electrospray ionization) for MS analysis of organic compounds in blood and urine. High sensitivity and quantitation precision have been achieved for analysis of therapeutic and illicit drugs in 5 μL samples. Real-time chemical derivatization has been incorporated for analyzing anabolic steroids. The monitoring of enzymatic functions has also been demonstrated with the cholinesterase in wet blood. The reported work encourages future development of disposable cartridges highly functioning with simple operation, in replacement of traditional complex lab procedures for MS analysis of biological samples.

Mass spectrometry (MS) has been demonstrated as a powerful tool for chemical and biological analysis. The high specificity, high sensitivity and high precision in quantitation are achieved traditionally in laboratory by eliminating the matrix effect through sample extraction and chromatographic separation prior to the MS analysis. The development of ambient ionization, especially with the recent demonstration using the paper spray, has indicated a promising future for direct MS analysis of high quantitation performance but using highly simplified protocols consuming ultra-small amounts of samples. This would be extremely important for the translation of the MS analysis to out-of-lab applications, especially point-of-care (POC) diagnosis. The underlying principle for a successful development along this direction is to minimize the sample consumption and to achieve high efficiency in an integrated process for the analyte extraction and ionization. Slug flow microextraction (SFME) and nanoESI (electrospray ionization) can be combined to perform a one-step analysis of biofluid samples. Excellent sensitivity and high quantitation precision have been obtained with blood and urine samples of only 5 μL. More importantly, the SFME-NanoESI method demonstrated how to incorporate a variety of different processes using a simple device, including liquid-liquid extraction, internal standard (IS) incorporation, chemical derivatization or even enzymatic reactions, which are necessary for a high performance mass analysis.

All the experiments were carried out with a TSQ Quantum Access Max (Thermo Fisher Scientific, San Jose, Calif., USA). The bovine blood was purchased from Innovative Research Inv. (Novi, Mich., USA). The human pooled blood for enzymatic reaction study was purchased from BioreclamationIVT (Baltimore, Md., USA). The synthetic urine was purchased from CST Technologies (Great Neck, N.Y., USA). The steroids were purchased from Steraloids Inc. (Newport, R.I., USA). All other chemicals were purchased from Sigma-Aldrich (St. Louis, Mo., USA).

Figure 11:
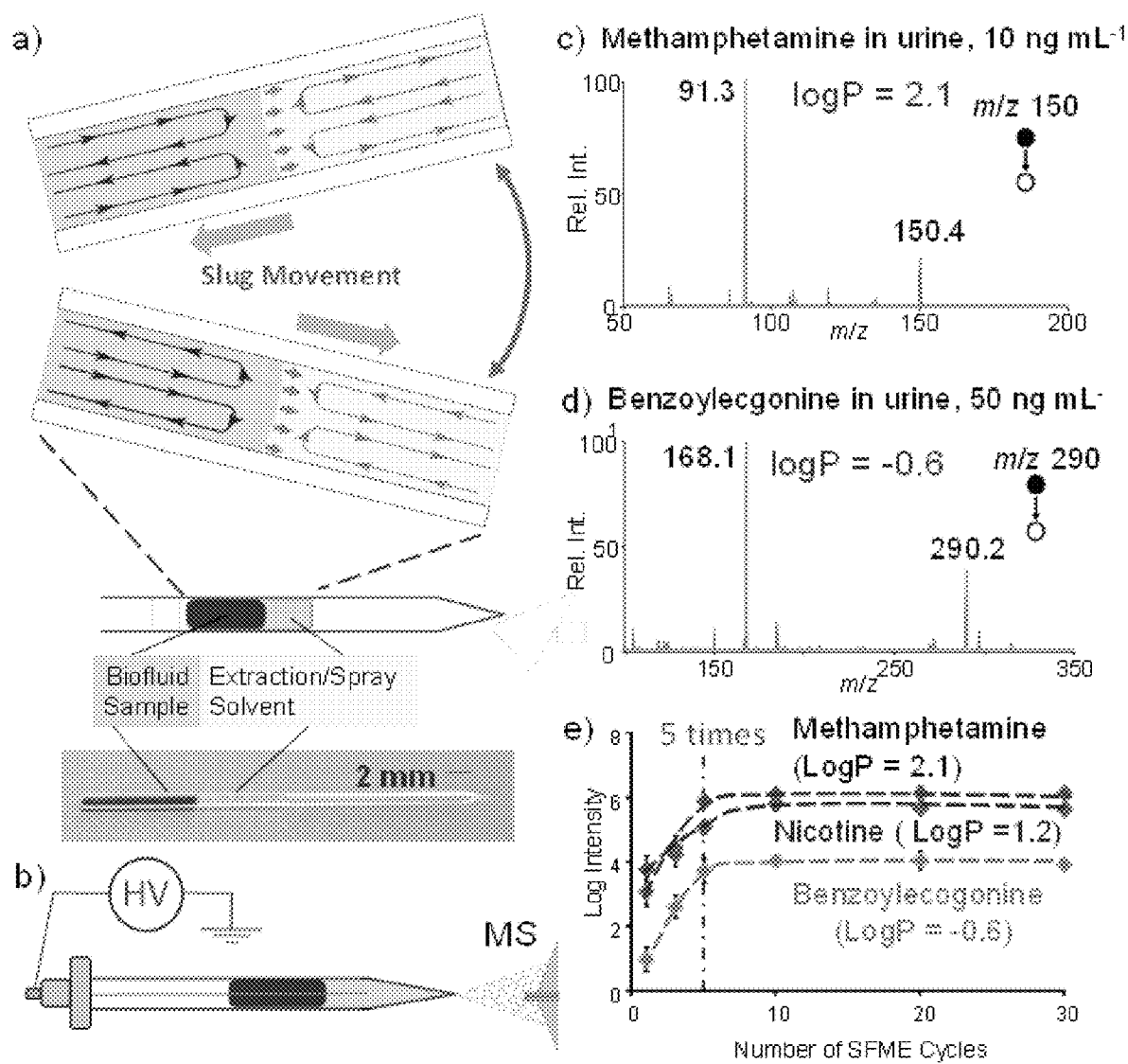
FIG. 11 panel A shows in-capillary sample extraction using the slug flow micro-extraction.
Figure 12:
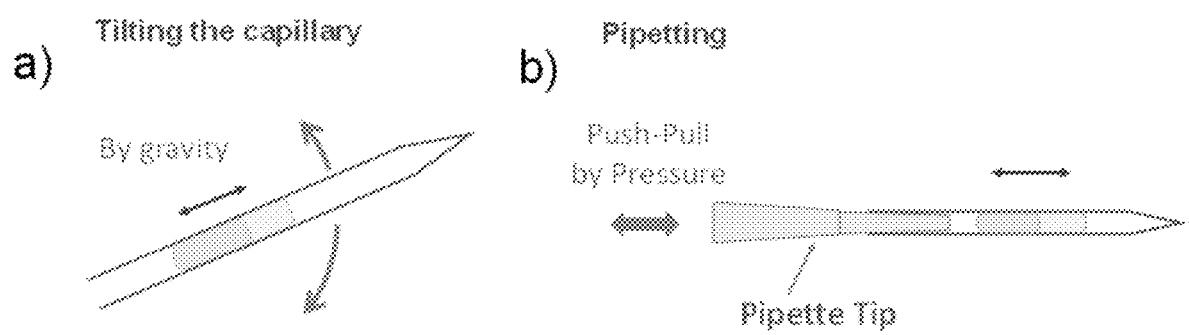
FIG. 12 panels A-B show that the movements of liquid plugs inside the capillary could be created in two ways.
Figure 13:
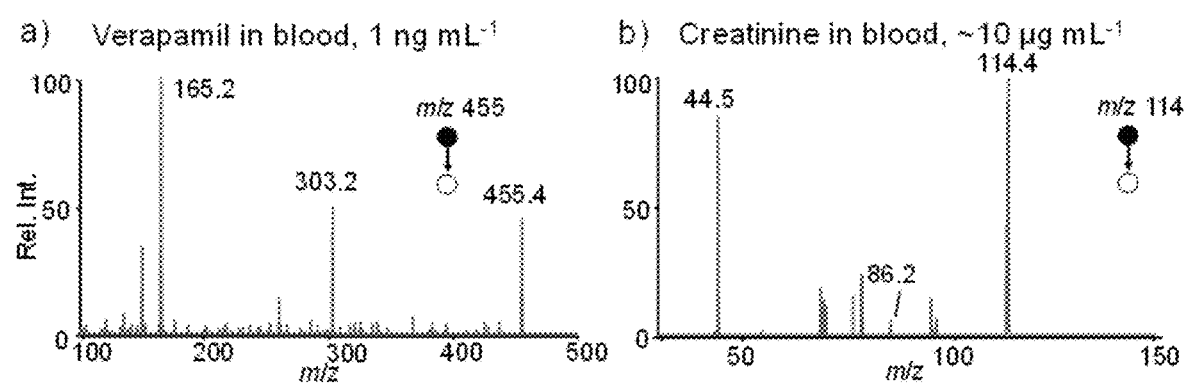
FIG. 13 panels A-B show spectra recorded for direct MS/MS analysis.

A disposable glass capillary of 0.8 mm i.d. (FIG. 11 panel A) with a pulled tip for nanoESI was used to perform the entire sampling ionization process. Two adjacent liquid plugs were formed by sequentially injecting 5 μL organic solvent and 5 μL urine or blood sample into the capillary. The liquid-liquid extraction of the analytes from the biofluid into the organic solvent is expected, but at a fairly low efficiency due to the small interfacing area. However, the extraction speed could be significantly improved with the slug flows induced by the movements of the two liquid plugs, which can be facilitated by tilting the capillary (FIG. 11 panel A and FIG. 12 panel A) or by applying a push-and-pull force through air pressure (FIG. 12 panel B). The slug flows is formed due to the friction with the capillary wall, and the flows inside each plug (FIG. 11 panel A) transfer the analytes to and away from the liquid-liquid interface, therefore significantly improving the extraction efficiency. After the extraction process, the organic solvent plug can be simply pushed to the tip of the capillary; a stainless steel wire was then inserted through the biofluid sample to reach the organic solvent plug; a high voltage was applied to generate the nanoESI for MS analysis (FIG. 11 panel B). The selection of the organic solvent is important. It should be immiscible with the biofluid samples, have good solubility for the target analytes and be suitable for nanoESI. Several organic solvents have been tested (FIG. 19) and ethyl acetate of a weak polarity was found to provide the optimal performance for analyzing a broad range of chemical compounds in urine (FIG. 11 panels C-D) and blood samples (FIG. 13 panels A-B).

Figure 20:
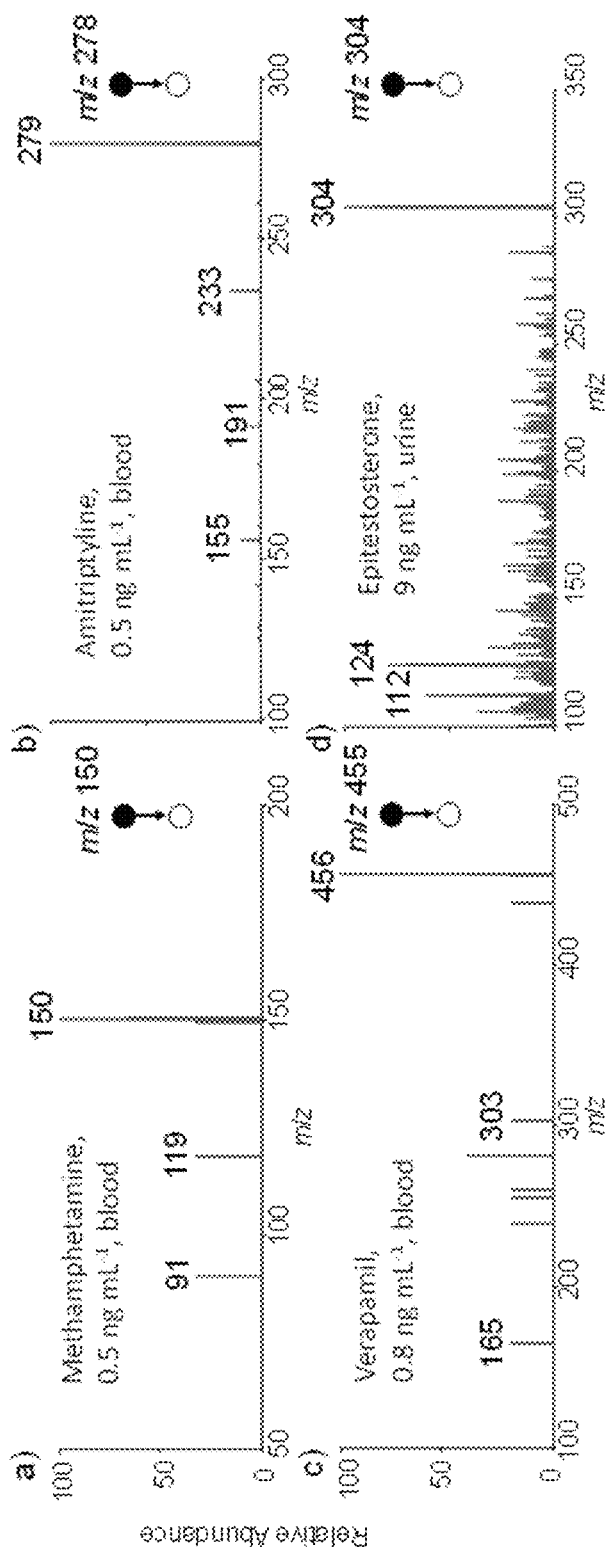
FIG. 20 panels A-D shows MS/MS analysis of drugs or steroids of low concentrations in 5 µL biological samples (undiluted).

The extraction process with the slug flows have been shown to be very efficient, as tested for extracting methamphetamine, nicotine and benzoylecgonine (a main metabolite of cocaine) from urine samples. The equilibrium was reached after tilting the capillary 5 times (FIG. 11 panel E and FIG. 20 panels A-D). Limits of detection (LODs) as good as 0.05 ng/mL for verapamil, have been obtained for the whole blood samples using SFME-nanoESI (Table 2).

TABLE 2

Limits of detection (LODs) for analytes in urine and/or whole

| Analyte | Sample | Derivatization | Sample Volume (µL) | LOD (ng/mL) |
|---|---|---|---|---|
| Methamphetamine | Urine | NA | 5 | 0.03 |
|  | Blood | NA | 5 | 0.1 |
| Benzoylecgonine LOD | Urine | NA | 5 | 0.1 |
|  | Blood | NA | 5 | 1 |
| Verapamil | Blood | NA | 5 | 0.05 |
| Amitriptyline | Blood | NA | 5 | 0.08 |
| Epitestosterone | Urine | Hydroxyl-amine | 5 | 0.7 |
| 6-Dehydro-cholestenone | Urine | Hydroxyl-amine | 5 | 0.6 |
| 5α-Androstan-3β,17β-Diol-16-one | Urine | Hydroxyl-amine | 5 | 0.2 |
| Stigmastadienone | Urine | Hydroxyl-amine | 5 | 0.8 |

Fewer extraction cycles were needed for reaching equilibrium if the blood samples were diluted to reduce the viscosity. The distribution of the analyte between the sample and extraction phase can be relatively estimated by the partitioning coefficient (logP, see FIG. 14). For methamphetamine with a logP of 2.1, its concentration in the organic extraction solvent can be 100 times higher than in the urine sample after SFME, which certainly explains the good LOD of 0.03 ng/mL achieved with urine samples (Table 1). The logP value for benzoylecgonine is −0.6, which means it has higher solubility in urine than in organic solvents and the extraction into ethyl acetate was a dilution process; however, an LOD of 0.08 ng/mL was achieved regardless. This indicates that the limiting factor in the detection of the benzoylecgonine in raw urine samples might not be the absolute amount or concentration of the benzoylecgonine, but the interference by the matrix effects, such as the ionization suppression due to the high concentrations of salts in the urine sample. An efficient separation of the benzoylecgonine from the salts was achieved in the SFME process. Even with a lower benzoylecgonine concentration in the extraction phase, the ionization efficiency and the overall sensitivity of the analysis were improved significantly.

Figure 15:
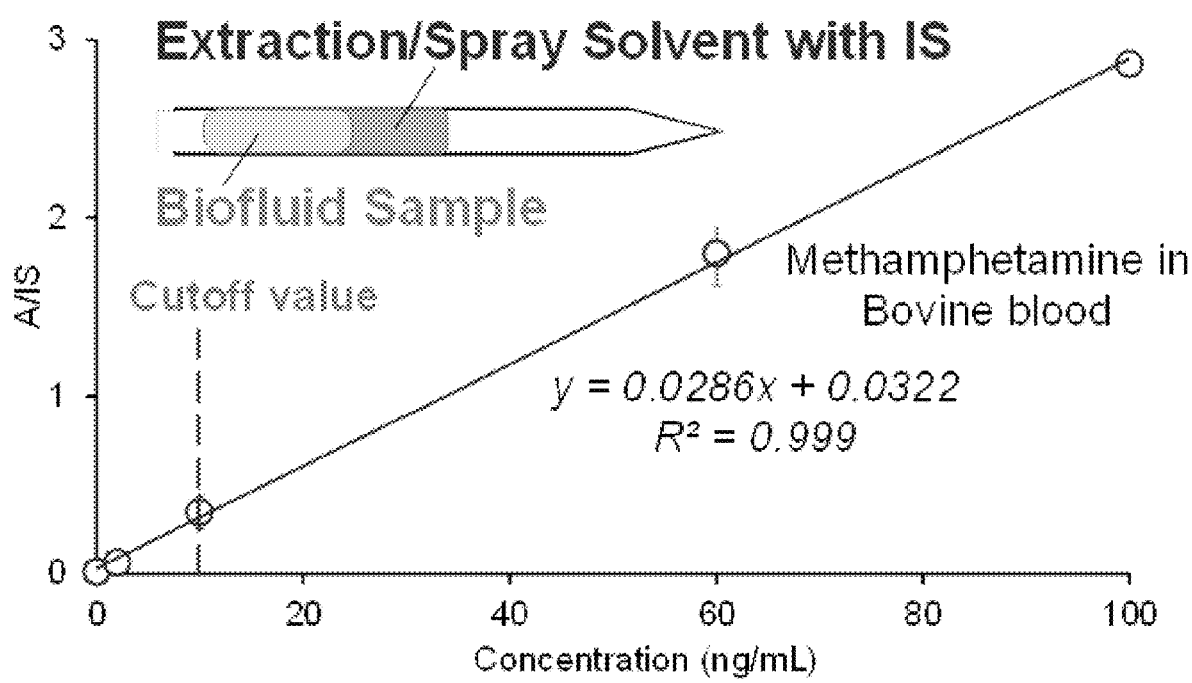
FIG. 15 shows quantitative analysis of whole blood spiked with methamphetamine (1-100 ng mL$^{-1}$). The blood samples were diluted 10 times for decrease in viscosity. Methamphetamine-d8 (2 ng mL$^{-1}$) in extraction solvent ethyl acetate.

In addition to the sensitivity, adequate precision in quantitation is often mandatory for clinical and POC applications. Simple means for accurate incorporation of internal standard are important but can be challenging for samples of small volumes taken by minimally invasive methods. Using the SFME-nanoESI, the IS compounds could be spiked in the extraction phase (FIG. 15) and subsequently mixed with the analyte during the slug flow extraction process. This method was tested for quantitation of methamphetamine in bovine blood samples with methamphetamine-d8 as the IS spiked in ethyl acetate at 2 ng/mL. The blood samples were diluted 10 times and then analyzed using the SFME-nanoESI and MRM analysis (transitions m/z 150 to 91 and m/z 158 to 94 for the analyte and IS, respectively) (FIG. 15, inset). The measured analyte-to-IS ratios (A/IS) are plotted as a function of the original analyte concentration in blood as shown in FIG. 15. A good linearity was obtained, which is governed by the partitioning process (see derivation in Supporting Information). RSDs better than 10% were obtained for samples of concentrations higher than 10 ng/mL.

Figure 16:
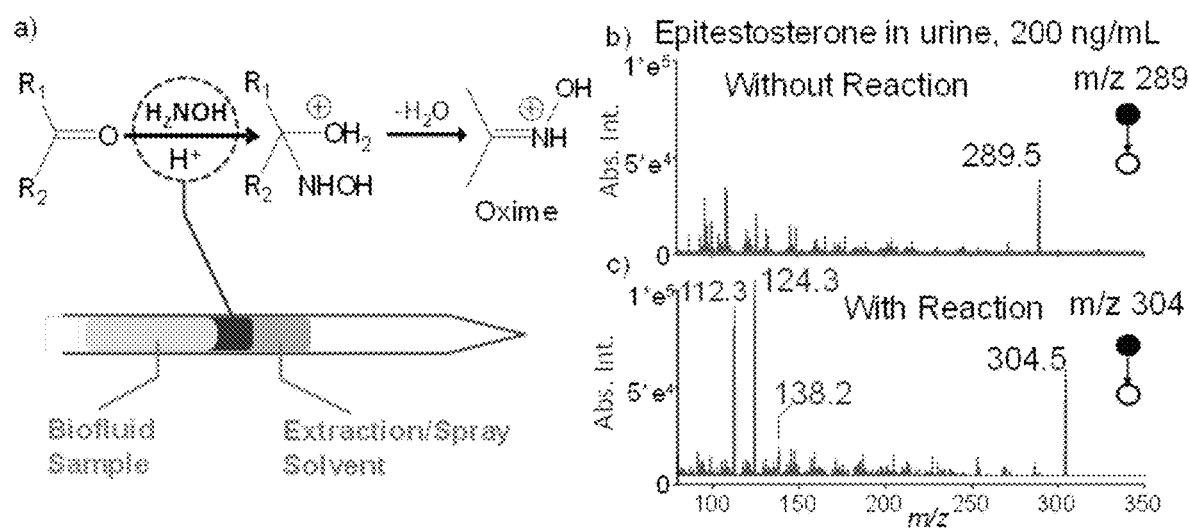
Figure 21:
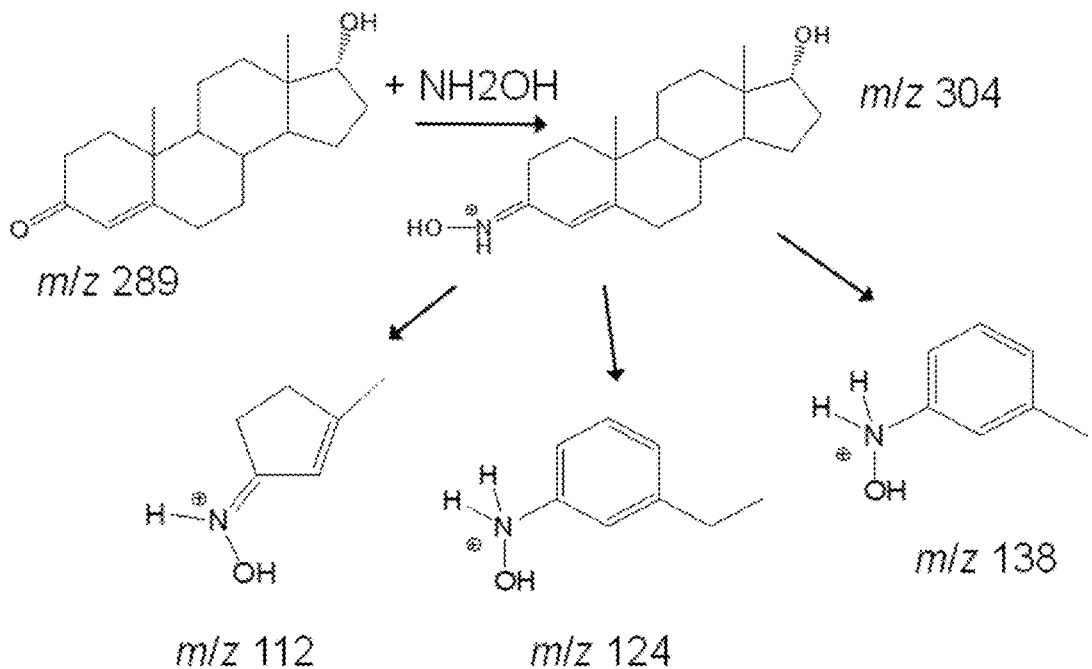
FIG. 21 shows derivatization and MS/MS fragmentation pathways of epitestosterone as well as a Table that provides a summary of the target ions for MS/MS analysis of steroid using reactive SFME-nanoESI.

Chemical derivatization is an effective way of altering the properties of the target analytes to improve the efficiency of separation or ionization for MS analysis. For example, the steroids in urine or blood samples are expected to be well extracted into an organic phase using the SFME; however, the efficiency for the subsequent ionization by nanoESI would be low due to the low proton affinity of the steroid molecules. The reaction with hydroxyl amine has previously been proved to be effective in improving the ionization efficiency of the steroids, and thereby was used in this study as an example. An additional liquid plug of 5 µL water containing 50 mM hydroxyl amine was injected between the 5 µL ethyl acetate and 5 µL urine sample spiked with 200 ng ml$^{-1}$ epitestosterone (FIG. 16 panel A). With 5 SFME cycles, the hydroxyl amine solution mixed well with the urine sample. The MS/MS analysis of the reaction product m/z 304 produced spectra of significantly improved signal-to-noise ratios (S/Ns) (FIG. 16 panels B-C and FIG. 21). The reactive SFME-nanoESI was applied for analysis of a series of anabolic steroids in 5 µL urine samples, including epitestosterone, 6-Dehydrocholestenone, 5α-Androstan-3β, 17β-Diol-16-one and stigmastadienone, with LODs of 0.7, 0.6, 0.2 and 0.8 ng/mL obtained, respectively (Table 1 and FIG. 22).

Figure 17:
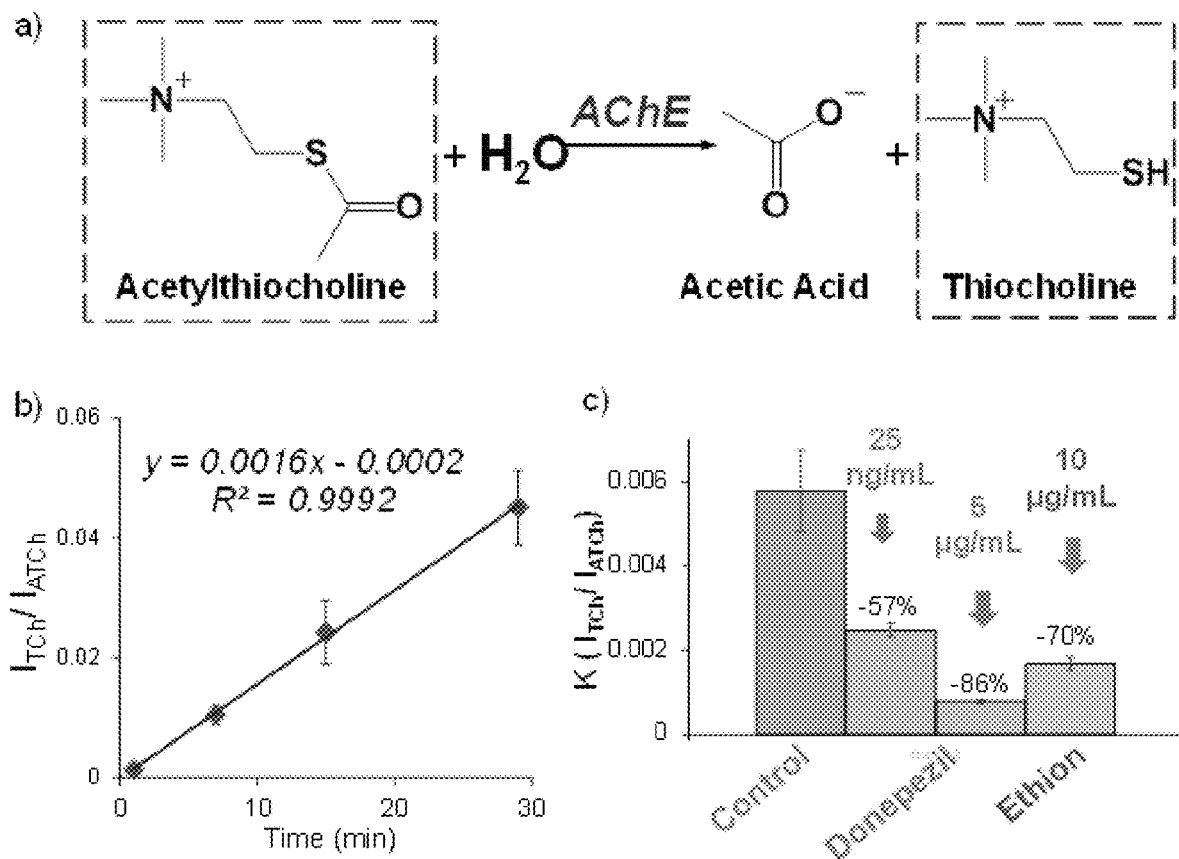
FIG. 17 panel A shows the reaction scheme of the enzymatic conversion of acetylthiocholine (ATCh) to thiocholine (TCh) catalyzed by cholinesterase (ChE).

Using the liquid-liquid extraction process with SFME, the analysis can now be performed directly with wet blood samples. This provides an opportunity for probing the chemical and biological properties that only exist with the original liquid samples. For instance, the enzymatic functions of the proteins are typically quenched in the dried blood spots or after the traditional lab procedure for sample extraction. SFME-nanoESI was applied for monitoring the enzymatic activity of cholinesterase (ChE) in whole blood samples. The ChE facilitates the enzymatic conversion of acetylthiocholine (ATCh) to thiocholine (TCh) (FIG. 17, panel A). The blood sample was diluted 10 times to slow down the reaction rate as well as to facilitate the slug flows for SFME. The substrate acetylthiocholine iodine was added into the diluted blood sample at a concentration of 1.8 mg/mL, and then 5 µL sample was taken immediately and injected into the capillary with 5 µL extraction phase. The capillary with the sample and the extraction solvent was left in room temperature 25° C. for incubation. The SFME-nanoESI could be performed repeatedly on the same sample and the ratio of the substrate ATCh and the reaction product TCh could be monitored as a function of time to characterize the enzymatic activity of the ChE. A potential problem in this approach would be the damage to the enzyme function by the organic solvent. The impact by organic extraction phase was investigated for ethyl acetate and other solvents such as chloroform with a 5 min incubation. It was found that the reduction of ChE activity due to the contact with ethyl acetate was minimal but much more severe (more than 60% decrease) with chloroform. A weakly polar solvent like ethyl acetate can better preserve the enzyme structures.

Using ethyl acetate as the extraction solvent, the SFME-nanoESI was performed repeatedly over 30 min, with 5 cycles for SFME and 5 s nanoESI at 1500 V for each analysis. The TCh/ACTh ratio is plotted as a function of time in FIG. 17 panel B, which is characteristic for the enzymatic activity of the ChE. An enzyme inhibition study was then carried out as a validation of this method. Two ChE inhibitors, donepezil (a therapeutic drug for Alzheimer's disease) and ethion (a neuron toxicant), were spiked separately into blood samples, simulating the enzyme inhibitions at different degrees. The compromised enzyme activities were then determined using the SFME-nanoESI method with 5 min incubation. In comparison with the blood samples without adding the inhibitors, the deficiencies measured are reported in FIG. 17 panel C for blood samples treated with donepezil at 25 ng/mL and 5 µg/mL, and with ethion at 10 µg/mL. The percent decreases observed are consistent with the findings reported for previous studies.

In summary, the combination of the slug flow microextraction with nanoESI enabled a high-sensitivity direct analysis of the organic compounds in biofluids. Multiple types of processes for sample treatments, which traditionally require complex setups in lab, can now be incorporated into a one-step analysis with extremely simplified operation procedure. Since the biofluid samples are directly analyzed without being made into dried spots, an efficient liquid-liquid extraction can be designed based on the partitioning properties. The chemical and biological properties of the wet biofluids can also be retained and characterized thereby. The extraction process can be turned on and off by controlling the movements of the sample and extraction plugs. This allows an on-line monitoring of the chemical and biological reactions in a biofluid sample of only 5 µL. With the increasing interest in the translation of MS technologies to the clinical applications, this development has a profound implication on designing disposable sample cartridges with adequate function for direct analysis. This could ultimately lead to an elimination of the traditional lab procedures requiring complex setups and expertise. Its implementation with miniature mass spectrometers would produce a powerful solution for POC diagnosis.

Example 10

Enzymatic Activity Monitoring by SFME-NanoESI

Figure 18:
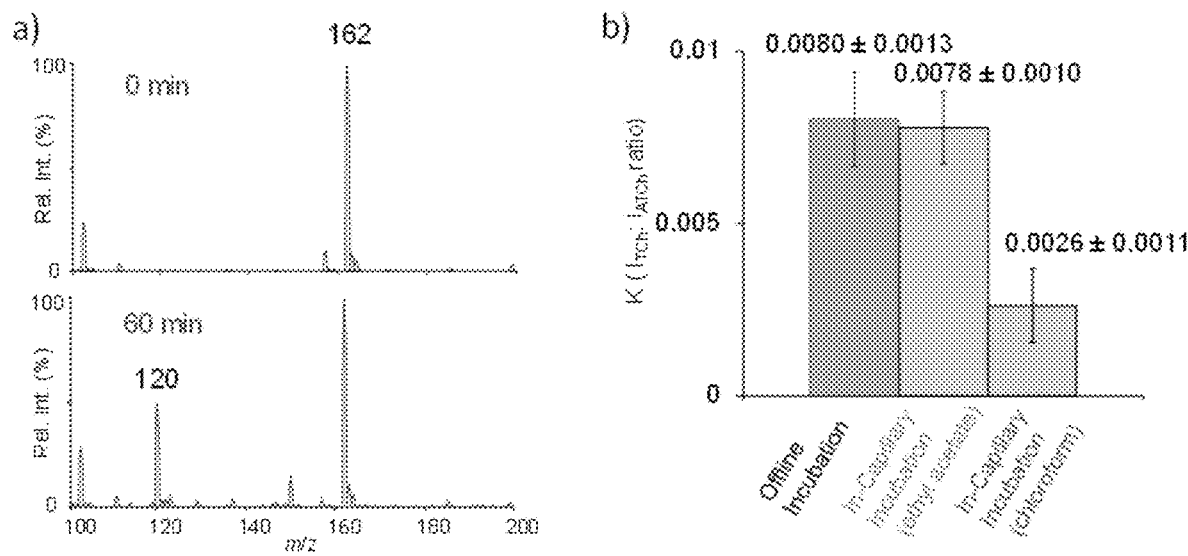
FIG. 18 panel A shows SFME-nanoESI-MS spectra recorded for SFME-nanoESI MS analysis of samples (54 µL each) taken immediately (top) and 60 min (bottom) after the mixing of the acetylthiocholine into the diluted blood.

For initiating an enzymatic reaction, acetylthiocholine (final concentration of 1.8 mg mL-1) was added into human blood sample, which had been diluted 10 times with phosphate buffered saline (PBS). For experiment producing the data for FIG. 17 panel B, 5 µL blood sample with acetylthiocholine added was loaded into a capillary along with 5 µL extraction solvent. Enzymatic reaction progress was determined by periodically performing the SFME-nanoESI MS analysis of the substrate (m/z 162) and the reaction product thiocholine (m/z 120) (FIG. 18 panels A-B). For each SFME-nanoESI MS analysis, the liquid plugs were pushed to let the extraction solvent reach the capillary tip for spray and then pulled back after the MS analysis. MRM was performed for measuring the intensities of TCh (m/z 120→61) and ATCh (m/z 162→102). The ratios of TCh/ATch are used for making the plot in FIG. 17 panel B. Three replicates were performed for each time point. The standard deviations are marked with the error bars in the FIG. 17 panel B.

Example 11

Bulk Sampling and Quantification

Figure 23:
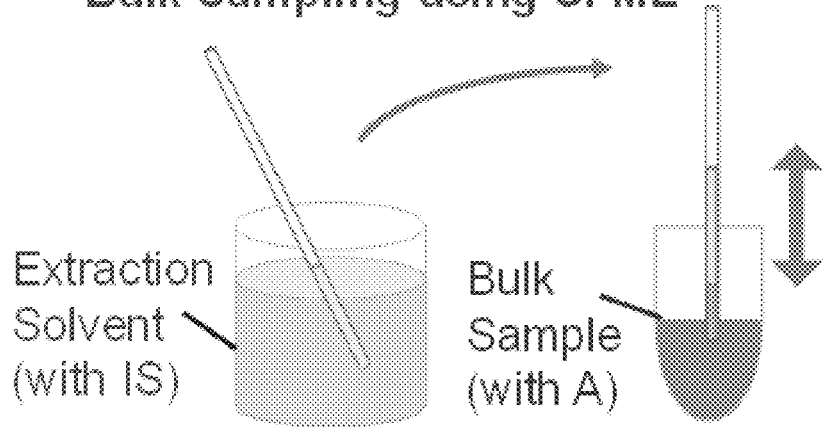
FIG. 23 shows an embodiment of SFME used for sampling of a bulk liquid sample (larger volume liquid sample, e.g., greater than 100 µl, in this example, a few milliliters).

The slug flow microextraction (SFME) has been demonstrated for extraction of analytes from samples of ultra-small volumes, such as 5 µL. This would be suitable for analyzing samples such as blood, which can be taken by minimally invasive means such as finger prick. For samples available at larger volumes, such as urine or environmental samples such as river water, SFME can also be used as shown in FIG. 23. The extraction solvent of small volume, such as 5 or 10 µL, is taken into the capillary. The solvent can optionally include an internal standard, as shown in FIG. 23. The solvent is either miscible or immiscible with the sample. In preferred embodiments, the solvent is immiscible with the sample. However, extraction and quantification methods are possible when the solvent and sample are miscible with each other. The capillary is then used to extract the analyte from a liquid sample of relatively large volume using slug flow microextraction as shown in FIG. 23. The extraction solution is then analyzed using nanoESI and a mass spectrometer, either sprayed from the capillary or transferred into a different hollow body for nanoESI.

The signal intensity of the analyte can be defined as:

$$I_a = k_a \cdot C_{a-e} = \frac{k_a V_s}{\frac{1}{D_a} \cdot V_s + V_e} \cdot C_{a-s}^o = \frac{k_a}{\frac{1}{D_a} + \frac{V_e}{V_s}} \cdot C_{a-s}^o \quad \text{Equation 1}$$

Where $k_a$ is the overall response constant, $C_{a-e}$ is the analyte concentration in the extraction solvent, $C_{a-s}^o$ is the original analyte concentration in the sample, $V_s$ and $V_e$ are the volume of the sample and extraction solvent, respectively, and $D_a$ is the ratio $C_{a-e}/C_{a-s}$ and $C_{a-s}$ is the analyte concentration in the sample after the extraction.

Figure 24A:
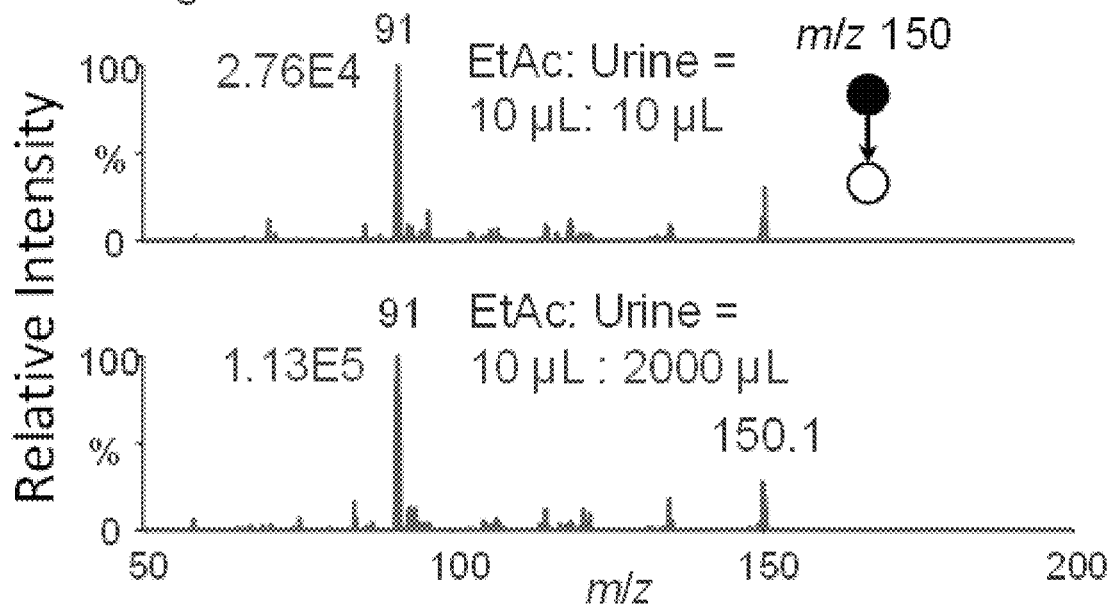
FIG. 24A shows a comparison of analyses of 5 ng/mL methamphetamine in 10 µL and 2 mL urine samples, 10 µL ethyl acetate used as extraction solvent.
Figure 24B:
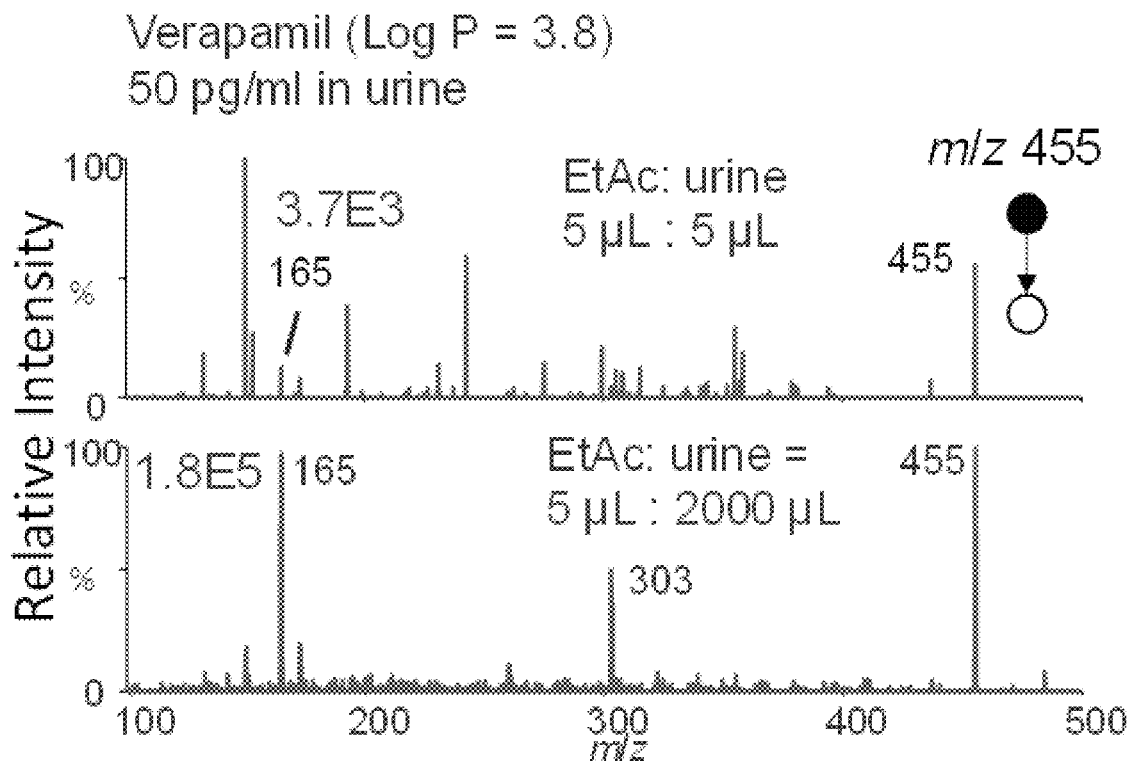
FIG. 24B shows a comparison of analyses of 50 pg/mL verapamil in 5 µL and 2 mL urine samples, 5 µL ethyl acetate used as extraction solvent.

A large volume of the sample may be helpful to improve the sensitivity of the analysis using SFME, as shown in FIGS. 24A-B. Higher intensities of the fragment ion peaks from the analytes were obtained with 2 mL samples, in comparison with 5 or 10 µL samples.

The signal intensity of the analyte can be defined as:

$$I_{IS} = k_{IS} \cdot C_{IS-e} = \frac{k_{IS} V_e}{\frac{1}{D_{IS}} \cdot V_s + V_e} \cdot C_{IS-e}^o = \frac{k_{IS}}{\frac{1}{D_{IS}} \cdot \frac{V_s}{V_e} + 1} \cdot C_{a-s}^o \quad \text{Equation 2}$$

The $I_a/I_{IS}$ ratio can be expressed as:

$$\frac{I_a}{I_{IS}} = \quad \text{Equation 3}$$

$$\frac{k_a \cdot C_{a-e}}{k_{IS} \cdot C_{IS-e}} = \frac{k_a}{k_s} \cdot \frac{\frac{1}{D_{IS}} \frac{V_s}{V_e} + 1}{\frac{1}{D_a} + \frac{V_e}{V_s}} \cdot \frac{C_{a-s}^o}{C_{IS-e}^o} = K \frac{\frac{1}{D_{IS}} \frac{V_s}{V_e} + 1}{\frac{1}{D_a} + \frac{V_e}{V_s}} \cdot C_{a-s}^o$$

When $D_a$ is relatively small and $$V_s \ll V_e, \frac{1}{D_a} \gg \frac{V_e}{V_s};$$

based on Equation 1, the variations in $V_e$ and $V_s$ (thereby $V_e/V_s$) has minimal impact on $I_a$. When $$\frac{1}{D_{IS}} \cdot \frac{V_s}{V_e} \ll 1, viz. D_{IS} \gg \frac{V_s}{V_e},$$

the variations in $V_e$ and $V_s$ (thereby $V_e/V_s$) has minimal impact on the $I_{IS}$ (Equation 2). When these conditions are met, high precision and accuracy of quantitation are obtained without requiring accurate or precise measurements of the $V_e$ and $V_s$. That is, quantification can be performed without knowledge of a volume of the sample and/or solvent.

Figure 25:
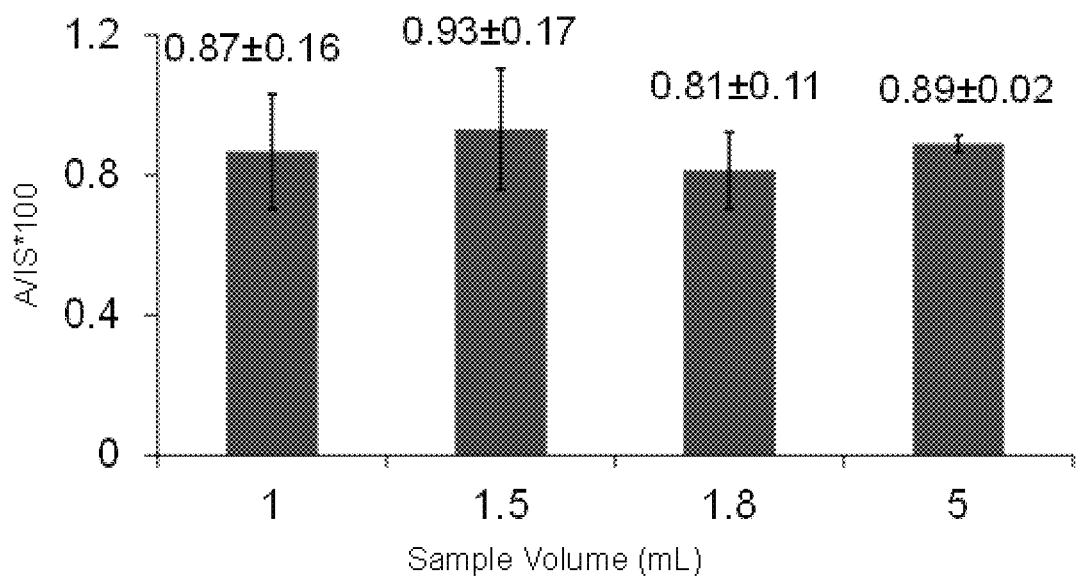
FIG. 25 is a graph showing the $$\frac{I_a}{I_{IS}}$$

For a demonstration, amitraz with high log P value (=5) was used as the Internal Standard (IS) for SFME analysis of cotinine (the analyte (A)) in urine samples. The $V_e$ was randomly selected between 6-9 µL for ethyl acetate containing 40 ng/mL amitraz (log P=5) as the extraction solvent. The $V_s$ of urine samples containing 300 ng/mL cotinine (log P=0.07) was selected as 1.0, 1.5, 1.8 and 5 mL. The measured $$\frac{I_a}{I_{IS}}$$

ratios are shown in FIG. 25. Relatively consistent ratio values were obtained regardless of the significant changes in the volumes of the extraction solvent and sample. The precision of the measured ratio is significantly better for a larger volume of 5 mL.

In another demonstration, calibration curve was established with a series of $$\frac{I_a}{I_{IS}}$$

measured for urine samples of different volume and containing cotinine (log P=0.07) at different concentration (see FIG. 26 inset). For each SFME, 10 µL ethyl acetate containing 5 ng/mL verapamil was used as the extraction solvent. Relatively good linearity was obtained, regardless the large variations in the sample volume.

It is an important advantage to perform quantitation of an analyte from a sample without requiring the control or knowing the volumes for the sample or the extraction solvent. This makes the on-site and in-field analysis extremely simple.

Example 12

SFME for Analysis of a Target Analyte from Blood

In another example, to extract biomarkers of relatively low polarities from blood samples, 5 µL sample and 5 µL organic solvent, such as ethyl acetate, were injected into a thin capillary. Efficient analyte extraction was achieved with the movement of the liquid plugs. LODs as low as 0.1 ng/mL have been achieved for analyzing drug compounds in urine and blood samples. For effectively extracting the tenofovir-diphosphate (TFV-DP) of high polarity from the whole blood lysate in this study, a 3-phase SFME is proposed as shown in FIG. 27A. The analytes are extracted from the polar blood lysate into a polar solvent, such as methanol:water (50:50), with a nonpolar bridge between them to prevent the salts and cell debris from being extracted. The extraction solvent can be analyzed using nanoESI directly or ESI through direct infusion. In a preliminary test, the 3-phase SFME was performed for analysis of 10 µL whole blood lysate containing 45 ng/mL TFV-DP. The extract was analyzed using a TSQ with nanoESI. The MS/MS spectrum was obtained with characteristic fragment ions m/z 149 and 79 at S/N better than 50 (FIG. 27B).

What is claimed is:

1. A method for extracting an analyte from a sample, the method comprising:
   estimating by a partitioning coefficient a distribution of an analyte between a sample and a solvent to thereby determine a solubility of a target analyte in a solvent;
   selecting the solvent that (i) will extract the target analyte from a sample into the solvent based on the target analyte being more soluble in the solvent than the sample and (ii) be compatible for ionization of the target analyte;
   introducing the solvent into a capillary;
   introducing the capillary into a vessel comprising the sample such that a portion of the sample is introduced into the capillary;
   moving the sample and the solvent within the capillary to induce circulation within the sample and the solvent, thereby causing the target analyte to be extracted from the sample and into the solvent, wherein the sample and the solvent do not mix with each other;
   analyzing the target analyte that has been extracted from the sample; and
   quantifying the target analyte.

2. The method according to claim 1, wherein the quantifying step is performed without knowledge of a volume of the sample.

3. The method according to claim 1, wherein the quantifying step is performed without knowledge of a volume of the solvent.

4. The method according to claim 1, wherein analyzing comprises:
   applying a voltage to the solvent comprising the extracted analyte in the capillary so that the analyte is expelled from the capillary, thereby generating ions of the analyte; and
   analyzing the ions.

5. The method according to claim 1, wherein analyzing comprises:
   removing the solvent comprising the extracted analyte from the capillary; and
   conducting an assay that analyzes the analyte.

6. The method according to claim 5, wherein the assay comprises:
   generating ions of the analyte; and
   analyzing the ions.

7. The method according to claim 1, wherein the solvent comprises an internal standard.

8. The method according to claim 1, wherein the sample comprises an internal standard.

9. The method according to claim 1, wherein the solvent is immiscible with the sample.

10. The method according to claim 1, wherein the solvent is miscible with the sample and the method further comprises introducing a bridging solvent into the capillary that is immiscible with the solvent and the sample in a manner in which the bridging solvent is between the solvent and the sample.

11. A method for extracting an analyte from a sample, the method comprising:
    estimating by a partitioning coefficient (LogP) a distribution of an analyte between a sample and a solvent to thereby determine a solubility of a target analyte in a solvent;

selecting the solvent that (i) will extract the target analyte from a sample into the solvent based on the target analyte being more soluble in the solvent than the sample and (ii) be compatible for ionization of the target analyte;

introducing the solvent into a capillary;

introducing the capillary into a vessel comprising the sample such that a portion of the sample is introduced into the capillary;

moving the sample and the solvent within the capillary to induce circulation within the sample and the solvent, thereby causing the target analyte to be extracted from the sample and into the solvent, wherein the sample and the solvent do not mix with each other.

12. The method according to claim 11, further comprising analyzing the extracted analyte.

13. The method according to claim 12, wherein analyzing comprises:

applying a voltage to the solvent comprising the extracted analyte in the capillary so that the analyte is expelled from the capillary, thereby generating ions of the analyte; and analyzing the ions.

14. The method according to claim 12, wherein analyzing comprises:

removing the solvent comprising the extracted analyte from the capillary; and conducting an assay that analyzes the analyte.

15. The method according to claim 14, wherein the assay comprises:

generating ions of the analyte; and analyzing the ions.

16. The method according to claim 11, wherein the solvent is introduced to the capillary first.

17. The method according to claim 11, wherein the sample is introduced to the capillary first.

18. The method according to claim 11, wherein the solvent comprises an internal standard.

19. The method according to claim 11, wherein the solvent is immiscible with the sample.

20. The method according to claim 11, wherein the solvent is miscible with the sample and the method further comprises introducing a bridging solvent into the capillary that is immiscible with the solvent and the sample in a manner in which the bridging solvent is between the solvent and the sample.

* * * * *